(12) United States Patent
Augustine et al.

(10) Patent No.: US 6,267,740 B1
(45) Date of Patent: *Jul. 31, 2001

(54) FLEXIBLE NON-CONTACT WOUND TREATMENT DEVICE WITH A SINGLE JOINT

(75) Inventors: Scott D. Augustine, Bloomington; John P. Rock, Minneapolis, both of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/514,499

(22) Filed: Feb. 29, 2000

Related U.S. Application Data

(63) Continuation of application No. 08/843,072, filed on Apr. 11, 1997, which is a continuation-in-part of application No. 08/342,741, filed on Nov. 21, 1994, now Pat. No. 5,817,145.

(51) Int. Cl.$^7$ .................................................. A61F 7/00
(52) U.S. Cl. .................. 602/2; 602/14; 602/41; 602/54; 607/114
(58) Field of Search .................. 602/2, 14, 41, 602/42, 54; 607/108, 114

(56) References Cited

U.S. PATENT DOCUMENTS

| 222,690 | 12/1879 | Goldschmidt . |
| 697,637 | 4/1902 | Lee . |

(List continued on next page.)

FOREIGN PATENT DOCUMENTS

| 269 938 | 7/1950 | (CH) . |
| 378 465 | 7/1964 | (CH) . |
| 31 02 674 | 9/1982 | (DE) . |
| 31 18 232 | 11/1982 | (DE) . |
| 35 39 533 | 5/1987 | (DE) . |
| 8305 103 | 4/1988 | (DE) ............................ A61F/13/00 |
| 0 355 186 | 2/1990 | (EP) ............................ A61M/27/00 |
| 0 424 165 | 4/1991 | (EP) . |
| 0 485 657 | 5/1992 | (EP) . |
| 0 607 472 | 7/1994 | (EP) . |
| 1 303 238 | 7/1962 | (FR) . |
| 1 489 127 | 7/1967 | (FR) . |
| 1 527 887 | 4/1968 | (FR) . |
| 2 544 202 | 10/1984 | (FR) . |
| 3090 | 6/1902 | (GB) . |
| 288 220 | 7/1927 | (GB) . |
| 2 082 919 | 3/1982 | (GB) . |
| 2 199 501 | 7/1988 | (GB) . |
| 2 261 822 | 6/1993 | (GB) . |
| WO 89 04158 | 5/1989 | (WO) . |
| WO 94 00090 | 1/1994 | (WO) . |
| WO 96 15745 | 5/1996 | (WO) . |

OTHER PUBLICATIONS

PCT/US 98/00344—Int. Filing date Jan. 14, 1998.
Carolyn Robinson et al, "Warm–Up Active Wound Therapy: A novel approach to the management of chronic venous stasis ulcers", *Journal of Vascular Nursing*, Jun. 1998, pp. 38–42.

*Primary Examiner*—Robert L. Nasser
(74) *Attorney, Agent, or Firm*—Gray Cary

(57) ABSTRACT

A non-contact wound treatment device suitable for releasable attachment to a patient's skin surface over a selected wound area in a non-contact position relative to the selected wound area, the wound treatment device comprising an attachment portion suitable for releasable attachment with the patient's skin surface, having an inner perimeter for defining the selected wound area, a wound treatment portion with a wound cover and a support member supporting the wound cover, and a transition portion with a joint connecting the wound treatment portion to the attachment portion.

12 Claims, 17 Drawing Sheets

U.S. PATENT DOCUMENTS

| | | |
|---|---|---|
| 720,812 | 2/1903 | Johnson . |
| 1,384,467 | 7/1921 | Homan . |
| 1,399,095 | 12/1921 | Webb, Sr. . |
| 1,777,982 | 10/1930 | Popp . |
| 1,920,808 | 8/1933 | Sander ................................. 128/154 |
| 1,979,082 | 10/1934 | Schwedenberg et al. ............. 219/46 |
| 2,221,758 | 11/1940 | Elmquist ............................. 128/154 |
| 2,443,481 | 6/1948 | Sene .................................... 128/155 |
| 2,573,791 | 11/1951 | Howells ............................. 128/82.1 |
| 2,577,945 | 12/1951 | Atherton ............................. 128/156 |
| 2,599,523 | 6/1952 | Dorr .................................... 128/153 |
| 2,601,189 | 6/1952 | Wales, Jr. ................................ 4/160 |
| 2,632,443 | 3/1953 | Lesher ................................ 128/156 |
| 2,706,988 | 4/1955 | Weber ................................. 128/102 |
| 2,769,892 | 11/1956 | Collins .................................. 219/46 |
| 3,026,874 | 3/1962 | Stevens ............................... 128/260 |
| 3,528,416 | 9/1970 | Chamberlain ...................... 128/154 |
| 3,596,657 | 8/1971 | Eidus .................................. 128/156 |
| 3,610,238 | 10/1971 | Rich, Jr. ............................. 128/184 |
| 3,610,251 | 10/1971 | Sanderson .......................... 128/379 |
| 3,687,143 | 8/1972 | Schneeberger et al. ............ 128/402 |
| 3,691,646 | 9/1972 | Ruffolo ................................. 34/90 |
| 3,782,377 | 1/1974 | Rychlik ............................... 128/132 |
| 3,814,095 | 6/1974 | Lubens ................................ 128/260 |
| 3,867,939 | 2/1975 | Moore ................................. 128/254 |
| 3,881,477 | 5/1975 | Von Otto ............................ 128/132 |
| 4,080,971 | 3/1978 | Leeper ................................ 128/383 |
| 4,134,399 | 1/1979 | Halderson .......................... 128/132 |
| 4,172,495 | 10/1979 | Zebuhr et al. ........................ 165/46 |
| 4,279,255 | 7/1981 | Hoffman ............................. 128/402 |
| 4,341,209 | 7/1982 | Schaar ................................. 128/156 |
| 4,382,441 | 5/1983 | Svedman ............................ 604/291 |
| 4,399,816 | 8/1983 | Spangler ............................. 128/154 |
| 4,468,227 | 8/1984 | Jensen ................................. 604/327 |
| 4,484,574 | 11/1984 | DeRusha et al. .................... 128/156 |
| 4,517,972 | 5/1985 | Finch, Jr. ............................ 128/156 |
| 4,540,412 | 9/1985 | Van Overloop ..................... 604/291 |
| 4,572,188 | 2/1986 | Augustine et al. .................. 128/380 |
| 4,628,930 | 12/1986 | Williams ............................. 128/379 |
| 4,633,863 | 1/1987 | Filips et al. ......................... 128/165 |
| 4,641,641 | 2/1987 | Strock ................................. 128/132 |
| 4,641,643 | 2/1987 | Greer .................................. 128/156 |
| 4,667,666 | 5/1987 | Fryslie ................................. 128/156 |
| 4,890,608 | 1/1990 | Steer ................................... 128/156 |
| 4,962,761 | 10/1990 | Golden ............................... 128/400 |
| 4,969,881 | 11/1990 | Viesturs ............................. 604/305 |
| 5,003,971 | 4/1991 | Buckley ............................. 128/156 |
| 5,025,777 | 6/1991 | Hardwick .......................... 126/263 |
| 5,060,662 | 10/1991 | Farnsworth, III ................... 128/888 |
| 5,086,763 | 2/1992 | Hathman ............................. 602/42 |
| 5,107,832 | 4/1992 | Guibert et al. ...................... 128/399 |
| 5,135,518 | 8/1992 | Vera ................................... 604/291 |
| 5,144,113 | 9/1992 | Hall et al. ........................... 219/549 |
| 5,144,958 | 9/1992 | Krueger et al. ..................... 128/743 |
| 5,170,781 | 12/1992 | Loomis ............................. 128/118.1 |
| 5,190,031 | 3/1993 | Guibert et al. ...................... 128/399 |
| 5,230,350 | 7/1993 | Fentress ............................. 128/846 |
| 5,431,622 | 7/1995 | Pyrozyk et al. ........................ 602/2 |
| 5,531,670 | 7/1996 | Westby et al. ........................ 602/41 |
| 5,580,346 | 12/1996 | Spier .................................... 602/42 |
| 5,609,619 | 3/1997 | Pompei .............................. 607/104 |
| 5,649,972 | 7/1997 | Hochstein ........................... 607/100 |
| 6,110,197 | * 8/2000 | Augustine et al. ..................... 602/2 |

* cited by examiner

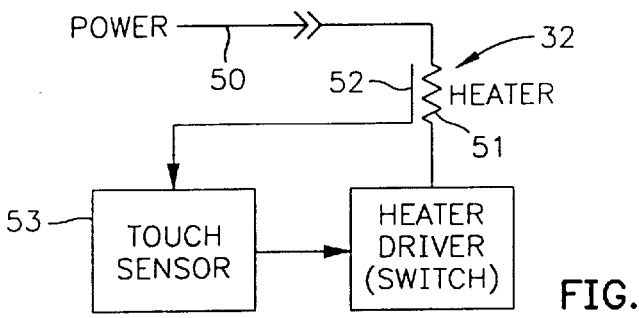
FIG. 8
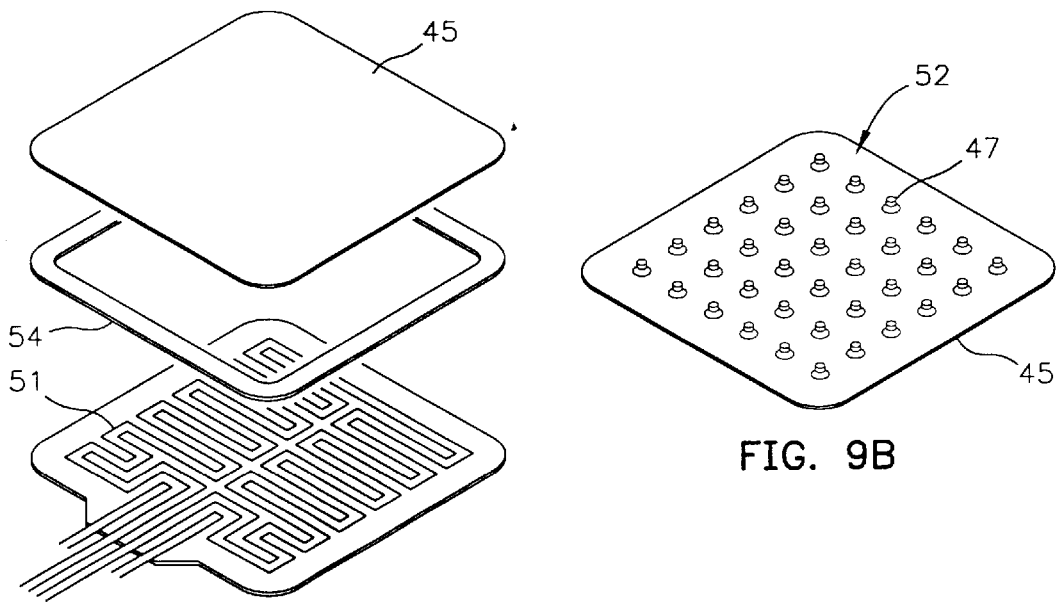
FIG. 9A
FIG. 9B
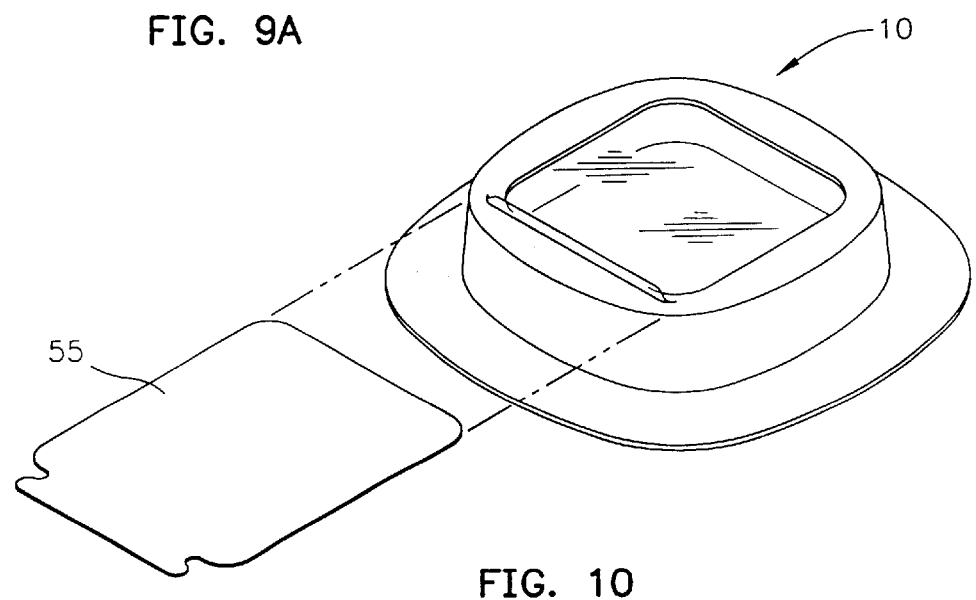
FIG. 10

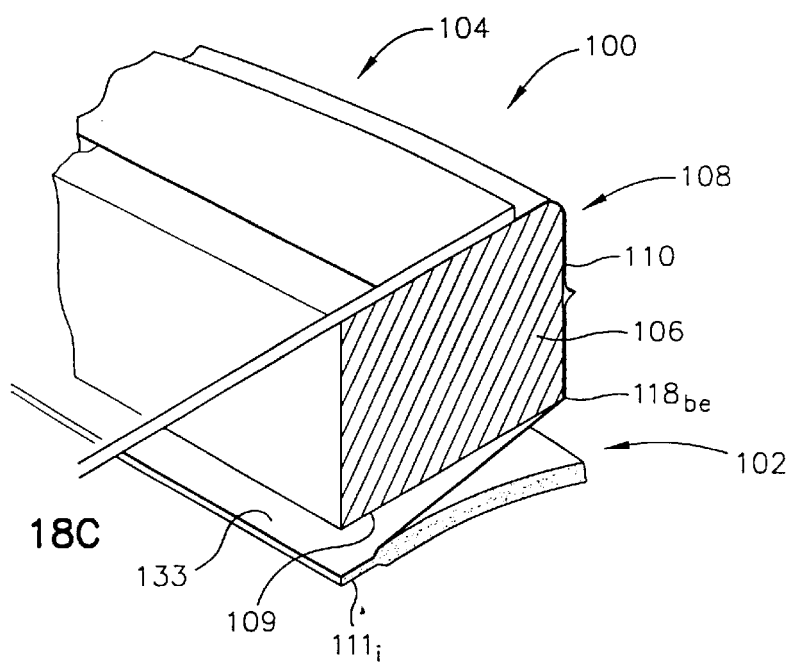
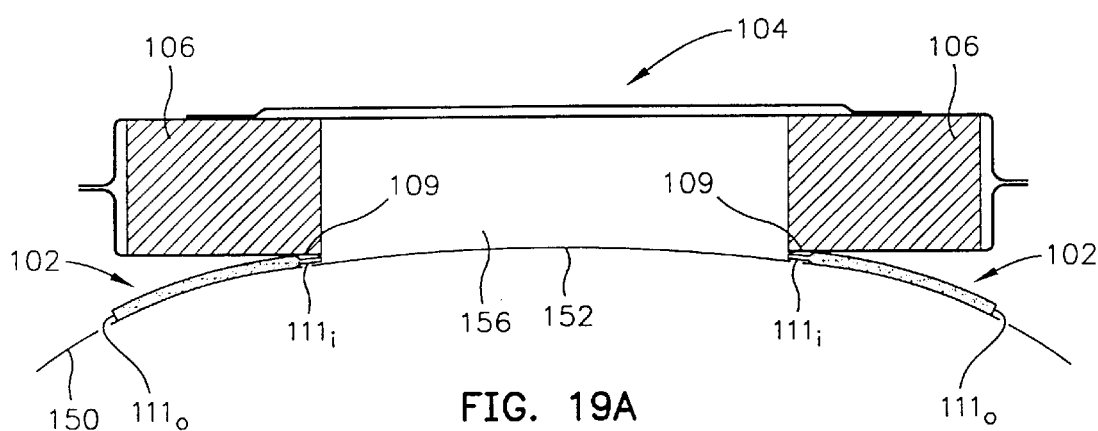
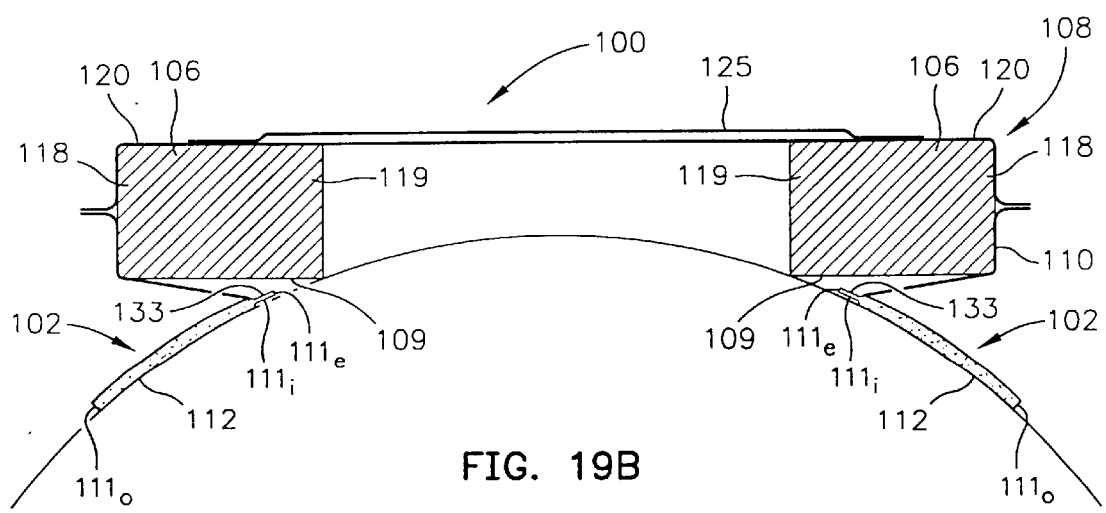

FLEXIBLE NON-CONTACT WOUND TREATMENT DEVICE WITH A SINGLE JOINT

CROSS REFERENCE TO RELATED CASES

This application is a continutation of Ser. No. 08/843,072 filed Apr. 11, 1997, which is a Continuation-in-Part of U.S. patent application Ser. No. 08/342,741, filed Nov. 21, 1994 now U.S. Pat. No. 5,817,145 titled WOUND TREATMENT DEVICE, assigned commonly with this application.

This application contains material related to the U.S. Patent application filed on even date herewith that is entitled "FLEXIBLE NON-CONTACT WOUND TREATMENT DEVICE" and to the following pending U.S. Patent applications all assigned commonly with this application:

Ser. No. 07/900,656, filed Jun. 19, 1992, for "THERMAL BODY TREATMENT APPARATUS AND METHOD";

Ser. No. 08/356,325, filed Feb. 21, 1995, for "WOUND COVERING";

Ser. No. 08/785,794, filed Jan. 21, 1997, for "NORMOTHERMIC HEATER WOUND COVERING";

Ser. No. 08/86,713, filed Jan. 21, 1997, for "NORMOTHERMIC TISSUE HEATING WOUND COVERING";

Ser. No. 08/786,714, filed Jan. 21, 1997, for "NEAR HYPOTHERMIC HEATER WOUND COVERING".

Technical Field

This invention relates to a wound treatment device and, in particular, to a wound treatment device having a substantial portion of a wound cover that is in non-contact with a wound and capable of delivering heat to the wound. More particularly, the wound treatment device includes such a wound treatment device with a single joint that maximizes the ability of the wound treatment device to adapt to the contours and movements of a human body.

BACKGROUND OF THE INVENTION

A novel mode of wound treatment is disclosed in detail in published PCT Applications WO 94/00090 and WO 96/15745, both owned in common with this application. This new treatment employs a non-contact wound treatment device that covers a wound, forming a treatment volume about and over the wound. An embodiment of such a wound treatment device may be characterized in having a plurality of parts, three of which are useful for the purpose of description. These three parts are an attachment portion, a wound treatment portion, and a transition portion. Each portion serves a respective function.

The attachment portion connects and retains the wound treatment device on the skin of a person. The wound treatment portion typically includes a standoff that rises above the person's skin surface, and a wound cover that spans an open portion of the standoff. Together, the standoff and wound cover define a wound treatment volume and a wound treatment area onto which the wound treatment volume is projected.

The transition portion connects the attachment portion to the wound treatment portion. An important function of the transition portion is to adapt the wound treatment device to the contour of the portion of a person's body where the device is mounted and to movements of the person's body that deform the wound treatment device in situ. In this regard, an important function of the transition portion is the accommodation of patient motion by the compliance of the transition portion.

Achievement of this important function of the transition portion is challenged by the need to maintain the orientation of the wound cover in the wound treatment portion —both in aspect and location —with respect to the wound being treated. The orientation of the wound cover is difficult to maintain when the wound treatment device is mounted on a highly curved part of a body. While the wound treatment devices disclosed in the referenced PCT applications exhibit excellent adaptability in a surface that is parallel to the surface of the body portion where the wound treatment device is mounted, there is impairment of adaptability and disturbance of the orientation of the wound cover due to limited flexibility in the direction of a Z axis that is perpendicular to the surfaces. If the transition portion is substantially perpendicular to the attachment portion, it may buckle in response to body motion or contour and collapse the standoff in the wound treatment portion. The collapse of the standoff of course alters the orientation of the wound cover with respect to the wound, possibly reducing the effectiveness of the wound treatment device.

Z axis conformability is especially important for a wound treatment device used on a portion of a person's lower leg. The lower leg has a very tight radius of curvature. Therefore, when a three-dimensional wound treatment device is curved around a lower leg, substantial stress results that may result in deformation of the shape of the wound treatment device, in some cases even causing the wound cover to contact the wound.

SUMMARY OF THE INVENTION

The overall flexibility of a wound treatment device is enhanced by an invention based upon the inventors' critical realization that provision of a joint in the transition portion that connects the wound treatment portion to the attachment portion accommodates patient motion and contour by providing articulation between these portions that permits flexion of the wound treatment device in all dimensions of the volume that the wound treatment device occupies.

In this invention, the joint connects the wound treatment portion to the attachment portion, extending between the standoff and the attachment portion. The joint attaches to the attachment portion under the standoff between inner and outer perimeters of the attachment portion.

Preferably, the inner perimeter of the attachment portion is limited to being contained within the outer perimeter of the standoff. This permits reduction of the size of the attachment portion, minimizing the total "foot print" of the wound treatment device. A smaller footprint is generally considered to be advantageous particularly when attaching the wound treatment device to a highly curved part of a person's body, such as the surface of a lower leg.

The joint, its connection of the standoff with the attachmnent portion, and its attachment to the attachment portion between inner and outer perimeters of the attachment portion provides a hinge-like operation that maximizes the adaptability of the wound treatment device and maintains the orientation of the wound cover over greater ranges of body curvature and movement than previously obtainable.

It is, accordingly, an objective of this invention to provide a flexible, non-contact wound treatment device that adapts to body curvature and motion.

Another objective is the provision of a non-contact wound treatment device having a wound treatment portion and an attachment portion, with a joint between the wound treatment and attachment portions.

It is a related objective in this latter regard to provide a joint between the wound treatment and attachment portions in the form of an accordion- or bellows-like member operating between the bottom of the standoff in the wound treatment portion and the attachment portion.

It is a further related objective to provide a joint between the wound treatment and attachment portions in the form of a seam joining these portions and permitting articulation therebetween.

A significant advantage of the invention is the potential reduction in size of the attachment portion, providing a smaller footprint of the wound treatment device.

BRIEF DESCRIPTION OF THE DRAWINGS

The various figures of the drawing depict illustrative and exemplary forms of the wound treatment device. Throughout the several views, identical reference characters represent similar or equivalent structures wherein:

FIG. 8 is an electrical schematic of a pressure sensitive switch for a heater system;

FIG. 9A is an exploded view of a pressure sensitive switch incorporated into a wound treatment device;

FIG. 9B is a view of a portion of the pressure sensitive switch;

FIG. 10 is a perspective view of a passive heater embodiment of the wound treatment device;

FIG. 18C is a magnified partial cross-sectional view of the embodiment of FIG. 15 showing further operation of the membrane in accommodating body motion;

FIG. 19A is a side elevational view of the cross-sectional view of FIG. 18B when attached to a human patient;

FIG. 19B is a side elevational view representing the cross-sectional view of FIG. 18C;

DETAILED DESCRIPTION

Figure 1:
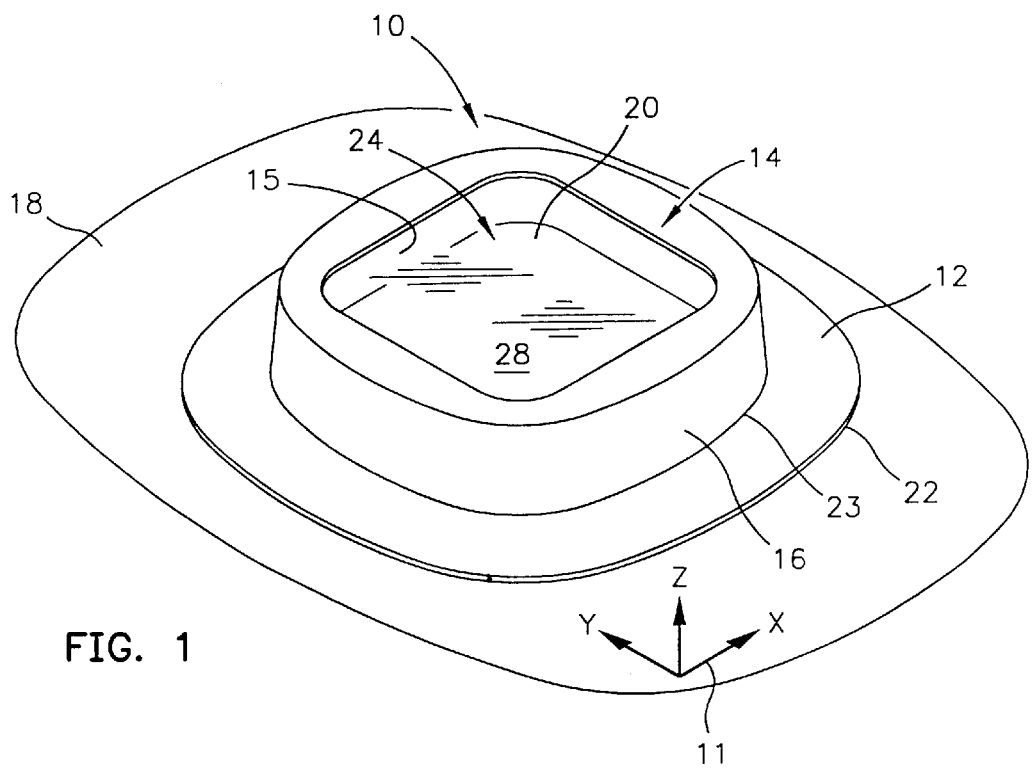
FIG. 1 is a perspective view of one embodiment of the wound treatment device.

For an understanding of the invention that is disclosed and claimed in this application, reference is made to FIGS. 1–10 in which embodiments and elements of a wound treatment device are illustrated. With reference especially to FIG. 1, a wound treatment device 10 has a planar upper surface displaced above the skin surface of the patient or person having a wound that is being treated by application and operation of the device 10. The wound treatment device 10 further includes an attachment surface generally held in a plane or surface that is coincident with the plane or surface of the person's skin. Together these two surfaces define an enclosed, non-contact volume over a wound treatment site.

The wound treatment device 10 that is illustrated in FIG. 1 may be considered in a general way for the purpose of description. In this regard, the description of a wound treatment device is aided by considering three separate parts of the wound treatment device 10. These parts are an attachment portion 12, a wound treatment portion 14, and a transition portion 16. Each portion is designed to serve a separate f unction.

The attachment portion 12 is used to connect the wound treatment device 10 to the skin of a patient. The wound treatment portion 14 of the wound treatment device 10 defines a vertical extent or dimension of the wound treatment device 10, and thus defines the location of the attachment surface. The transition portion 16 connects the attachment portion 12 to the wound treatment portion 14. The transition portion 16 is provided to improve the comfort and utility of the wound treatment device 10 when the patient moves and stretches the device.

FIG. 1 is a perspective view of a wound treatment device 10 applied to a patient's skin surface 18. A coordinate system 11 is depicted on the patient's skin surface 18 and it defines X, Y and Z directions. An attachment portion 12 is formed as an planar rim or flange. This attachment portion 12 is attached to the patient's skin 18 with an adhesive and it lies in a first XY plane. In this embodiment of wound treatment device 10, a transition portion 16 is integrally formed with attachment portion 12. Transition portion 16 rises from the skin surface in the Z direction to connect to a wound treatment portion 14. In this embodiment, wound treatment portion 14 has a transparent planar wound cover 20 which allows one to see a wound treatment area 28. Wound cover 20 is supported above the first XY plane by a foam ring standoff 15. Wound cover 20 lies in a second XY plane that is vertically displaced along the Z-axis by foam ring standoff 15 from the first XY plane. Wound cover 20 and foam ring standoff 15 together form wound treatment portion 14. The region over wound treatment area 28 is called a wound treatment volume 24.

In this figure, wound treatment device 10 has been applied to a patient's skin and is in a relaxed state. In this unstressed state one can see an outer periphery 22 of attachment portion 12. An inner periphery 23 is shown by a crease in the structure where it connects to transition portion 16.

Figure 2:
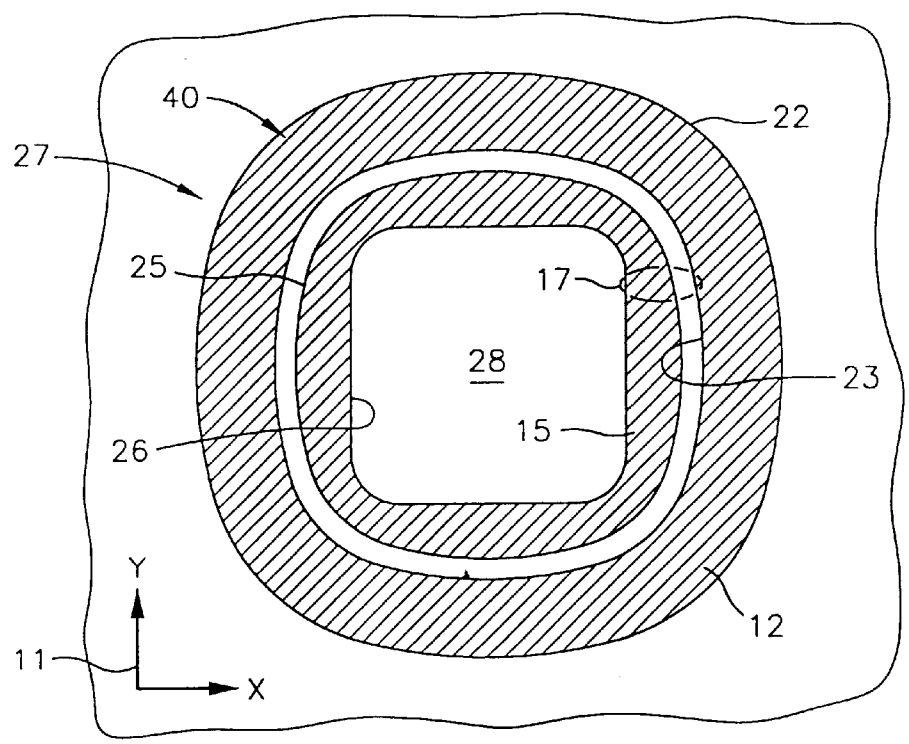
FIG. 2 is a schematic view of projected areas.
Figure 3:
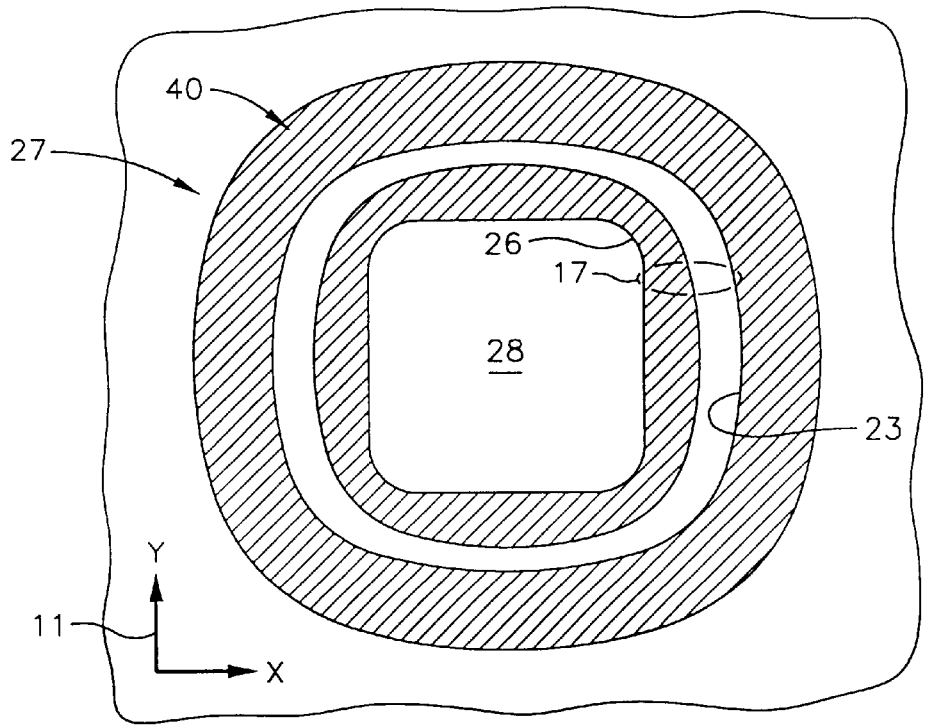
FIG. 3 is a schematic view of projected areas.

FIG. 2 and FIG. 3 should be considered together where they show the influence of patient motion on wound treatment device 10. Both FIG. 2 and FIG. 3 are top views of wound treatment device 10 of FIG. 1 with the various portions of wound treatment device 10 projected onto the first XY plane.

In FIG. 2, the wound covering is shown in a relaxed and un-stretched state having a nominal total projected area 27. Projected wound treatment area 28 is shown at the center of the wound treatment device 10. The outline of foam ring standoff 15 may be seen as the crosshatch area bounded by an exterior perimeter 25 of foam ring standoff 15, and an interior perimeter 26 of foam ring standoff 15. A transition portion projected area 17 is bounded by inner periphery 23 of attachment portion 12, and interior perimeter 26 of foam ring standoff 15. An attachment portion projected area 40 is shown as that cross hatched area bounded by outer periphery 22 and inner periphery 23 of attachment portion 12.

FIG. 3 shows wound treatment device 10 stretched along the X-axis by patient motion. In comparison to FIG. 2, the overall or total projected area 27 of wound treatment device 10 has increased. Attachment portion projected area 40 has increased slightly as attachment portion 12 moves with the underlying skin. Projected wound enclosure area 28 is essentially unchanged in area since in this embodiment foam ring standoff 15 is free move against the skin. The largest percentage area change occurs in transition portion projected area 17. As wound treatment device 10 deforms in response to patient motion, transition portion 16 is compliant and pays out material permitting the majority of the increase in total projected area 27 to be accommodated primarily by transition portion projected area 17.

Figure 4:
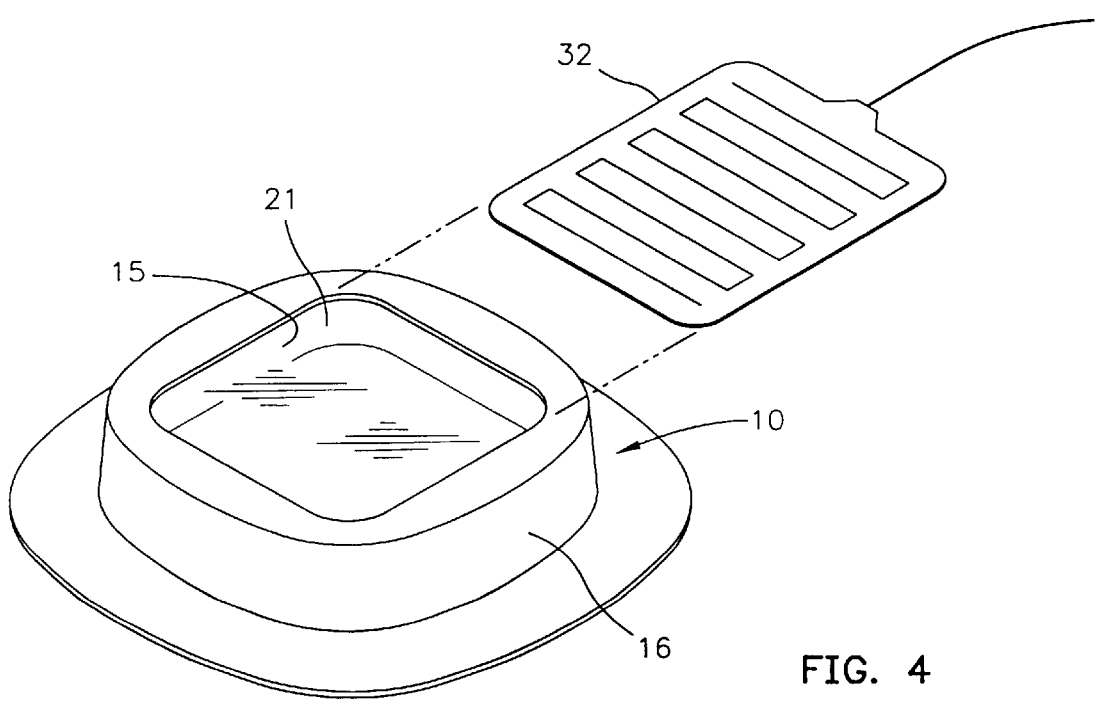
FIG. 4 is a perspective view of a detachable heater in combination with the one embodiment of a wound treatment device.

FIG. 4 shows a detachable heater 32 positioned for insertion into a pocket formed by pocket cover 21. Pocket cover 21 is bonded to wound cover 20 and is sized to retain heater 32. Foam ring standoff 15 and wound cover 20 serve to stabilize the shape of wound treatment device 10 while transition portion 16 accommodates patient motion. Consequently, heater 32 is reliably and comfortably positioned above the wound surface. In general, it is desirable to use a planar heater as heater 32 which has a prescribed heat output per unit area. This form of heater results in a more uniform flux of radiant energy applied to the wound. The amount of heat supplied to the wound area is largely independent of the height of heater 32 above the wound surface within the range of finctional heights of this device. In some cases, non-uniform wound area heating might be desirable and therefore the watt density of the heater may be non-uniform across its surface.

Figure 5:
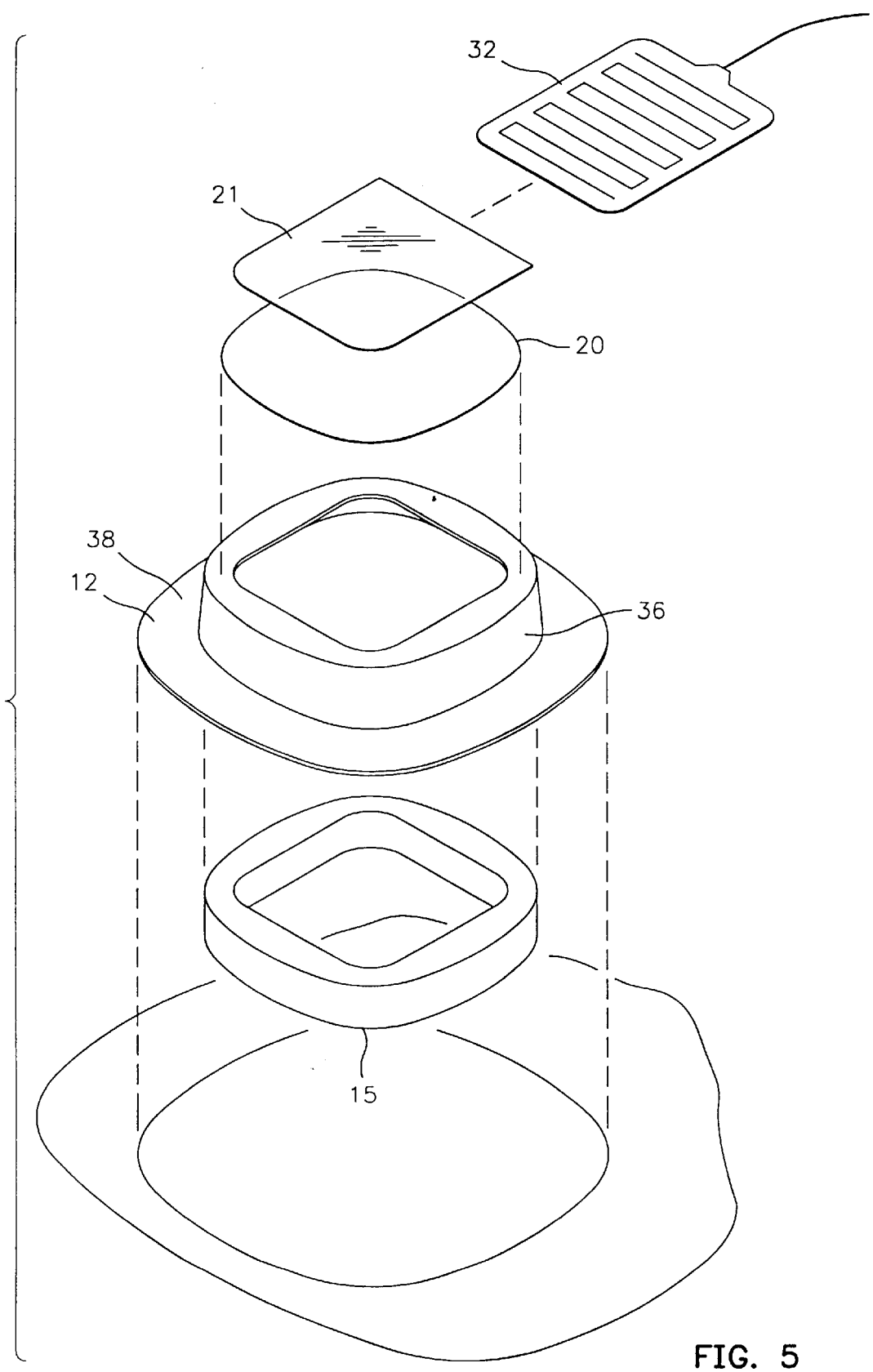
FIG. 5 is an exploded view of the one embodiment of a wound treatment device.

FIG. 5 is an exploded view of the first embodiment of wound treatment device 10. Attachment portion 12 and transition portion membrane 36 are formed as a unitary composite shell 38. Composite shell 38 may be vacuum formed from closed cell polyolefin foams such as Volara-6AS, which is a polyethylene material as sold by Illbruck Inc., of Minneapolis, Minn. It should be apparent that many other materials may be substituted within the scope of the invention. Foam ring standoff 15 may be die cut from foam sheeting of a reticulated polyurethane foam. The absorbency of the foam as well as its mechanical properties can be tailored to the particular wound treatment application. For example, the foam standoff may be impregnated with a medicament such as an antibiotic, antifungal, or antimicrobial material. It may also be desirable to supply a deodorant material or nitric oxide releasing material from the foam standoff. Wound cover 20 and wound pocket 21 may be made from a thin film of polyethylene. In general, the composite shell should be sufficiently self supporting so that when wound treatment device 10 is removed from its release liner, wound treatment portion 14 is held up or supported by the shaped flexion joint of transition portion membrane 36, and some effort is required to evert composite shell 38 and turn it inside out This behavior defines the self supporting feature which causes foam ring standoff 15 to lie gently against the skin even when wound treatment device 10 is upside down. For larger wound coverings it may be desirable to apply a tacky adhesive to the patient contact surface of the standoff.

Figure 6:
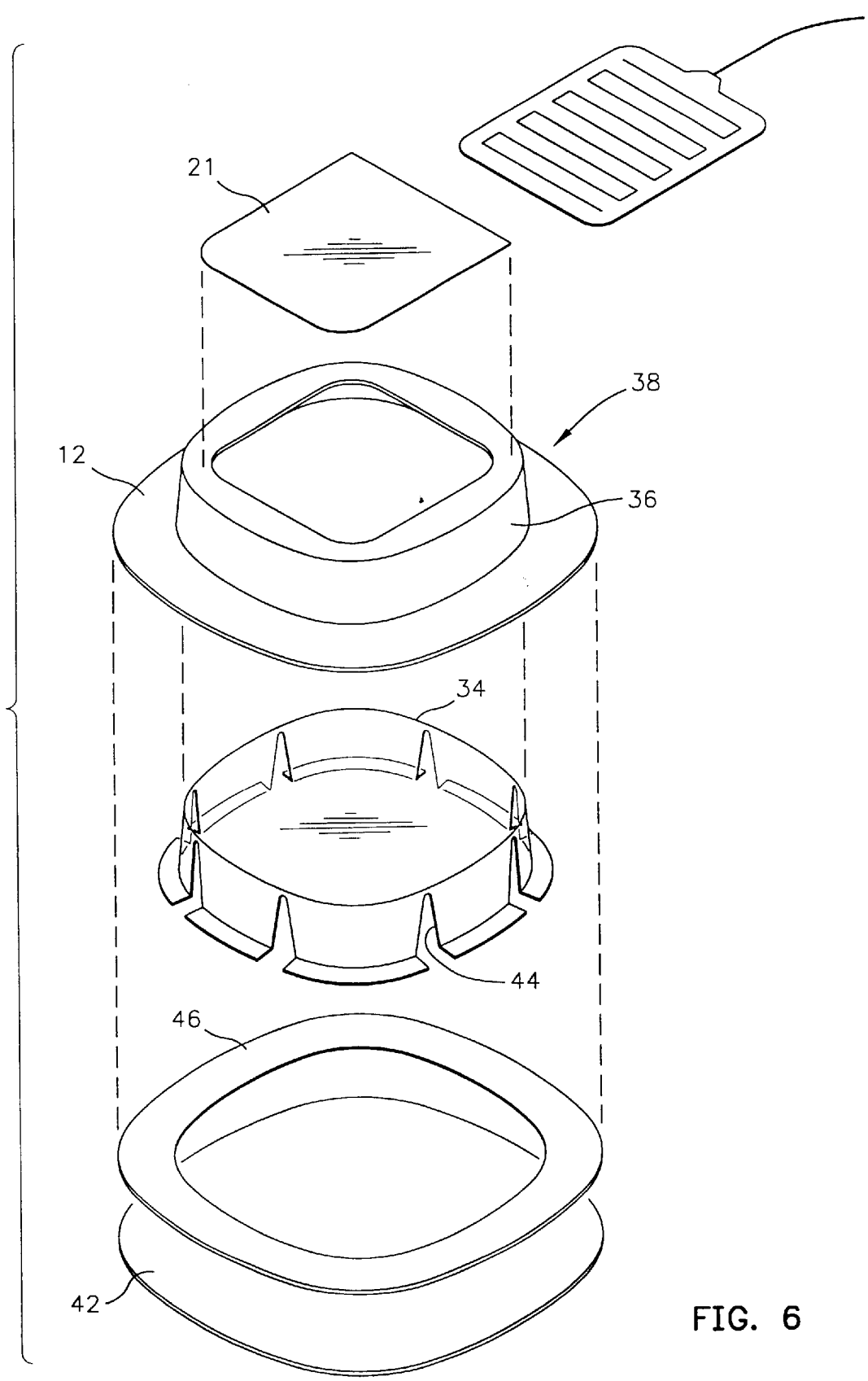
FIG. 6 is an exploded view of another embodiment of a wound treatment device.

FIG. 6 is an exploded view of another embodiment of wound treatment device 10. Attachment portion 12 and transition portion membrane 36 are formed as a unitary composite shell 38. In this embodiment, the wound treatment volume is defined by a serrated cup standoff 34. Standoff 34 may be made from a more rigid polymeric material, such as polyethylene, or the like. The serrations typified by a plurality of serrations 44 permit serrated cup standoff 34 to flex and accommodate patient motion. This embodiment shows a release liner 42 coupled to attachment portion 12 of composite shell 38 with an adhesive 46. In this embodiment, pocket cover 21 is bonded to composite shell 38.

Figure 7:
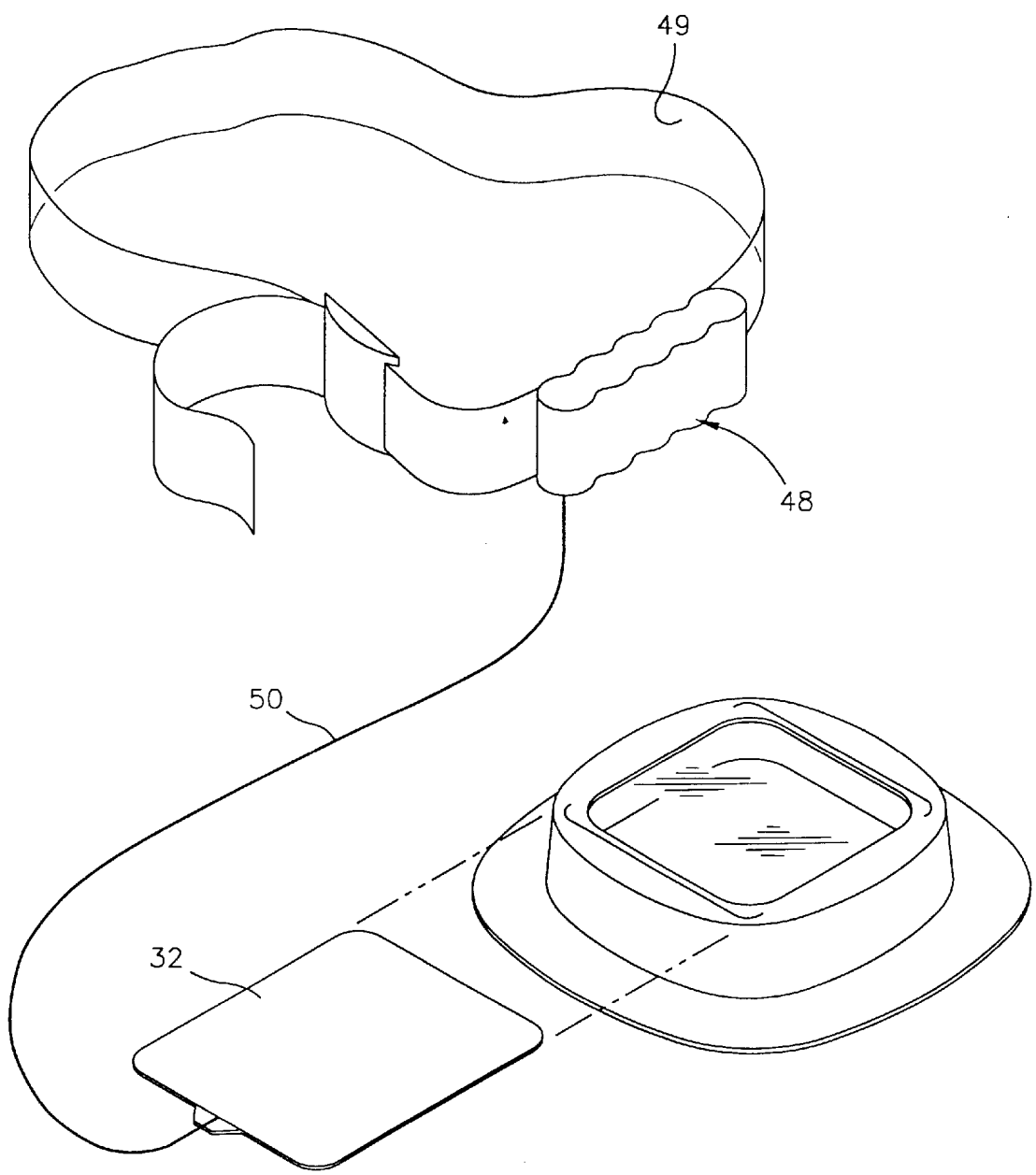
FIG. 7 is a perspective view of a heater system.

FIG. 7 depicts a portable power supply 48 to provide for the ambulatory use of the heated versions of the wound treatment device. A collection of battery cells may be wired together to form power supply 48 which may be conveniently attached to a belt 49. A suitable cable 50 may be used to conduct power to heater 32. In many instances, it may be desirable to cut off power to heater 32 if wound treatment device 10 is collapsed against the wound so as to prevent overheating of the wound surface.

FIG. 8 shows a schematic representation of a touch switch 52 which may be incorporated directly into detachable heater 32. Heater 32 includes a continuous resistive heating coil 51. A conductive membrane makes up touch switch 52 and is arranged near heating coil 51 so that it may "short out" segments or portions of coil 51 it touches. In use, all power to heating coil 51 is completely turned off by pressure applied to an entire touch sensor 53.

FIG. 9A shows an exploded version of heater 32 incorporating a touch switch 52 of the type described schematically in FIG. 8. A switch cover 45 has a conductive membrane which is located over the conductive pattern of heating coil 51. It is held in position with an adhesive band 54. FIG. 9B shows the underside of switch cover 45 showing a plurality of discrete insulation bumps typified by a bump 47 which serve to space and support touch switch 52 above heating coil pattern 51. Pressure supplied to switch cover 45 inactivates heater coil 51.

FIG. 10 shows an accessory device 55 or cover. This may take the form of a passive heater (or insulator) with a reflective surface facing the wound. Accessory device 55 may also take the form of a mapping grid where a grid work of lines is positioned on a transparent card to permit tracking of the wound healing process.

FIG. 11A through FIG. 11D should be considered together. These drawings facilitate a description of the connection of the various structures of the invention and represent several alternative connection geometries. In general, to accommodate patient motion, the transition portion pays out stored material to increase the projected area of the transition portion. Each of these drawings represents a mechanical schematic cross section of a wound treatment device 10 in the XZ plane. In each FIGURE, the wound covering is in the relaxed state.

Figure 11A:
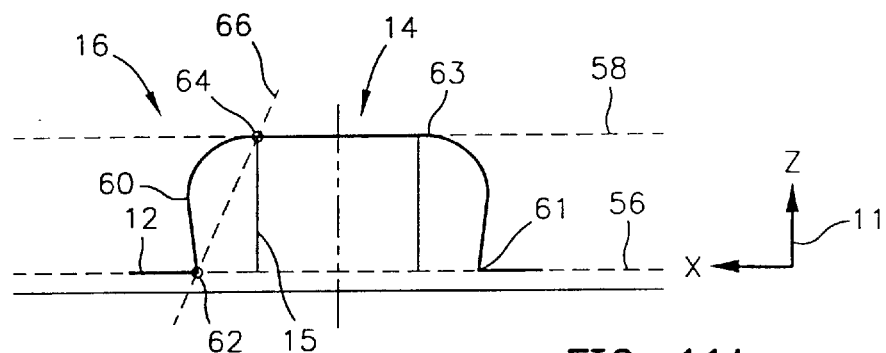
FIG. 11A is a schematic drawing depicting an alternate geometry for the transition portion.

FIG. 11A shows a schematic view of a ring standoff 15 extending from a first plane 56 to a second plane 58. Transition portion 16 has a transition portion membrane 60 which is coupled to attachment portion 12 by a first flexible connection 62 formed at the intersection of attachment portion 12 and transition portion 16. Transition portion membrane 60 is connected to treatment portion 14 at a second flexible connection 64 which is formed at the intersection of transition portion 16 and wound treatment portion 14. Wound treatment portion 14 is generally a cylindrical cup-shaped structure defining a wound treatment area on the patient skin surface. A minimum interconnection distance 66 is depicted as a dashed line extending from first flexible connection 62 to second flexible connection 64. The length of minimum interconnection distance 66 can be used to characterize the "length" of transition portion membrane 60. For many embodiments of the invention, the length of transition portion 16 between first flexible connection 62 and second flexible connection 64 is greater than the length of the straight line drawn between these points. This relationship is true for many embodiments of the wound treatment device when they are in the relaxed or unstressed position. It should be noted that the vertical distance between first plane 56 and second plane 58 represents a minimum value for minimum interconnection distance 66. In the XY plane, first flexible connection 62 forms a first perimeter 61 and a second perimeter 63. In the embodiment depicted in FIG. 11A, first perimeter 61 is larger than second perimeter 63.

Figure 11B:
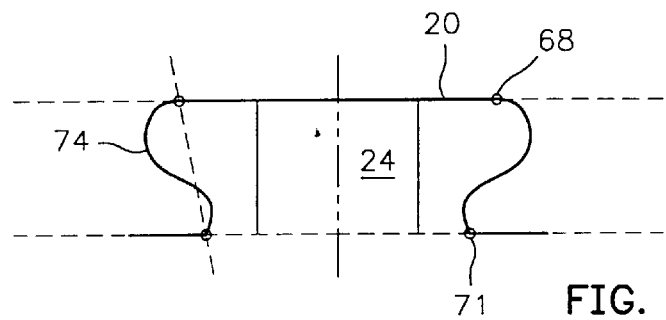
FIG. 11B is a schematic drawing depicting an alternate geometry for the transition portion.

FIG. 11B is a mechanical schematic diagram which represents a cross section of another embodiment of the wound treatment device 10 with an alternate connection geometry. In this drawing, wound cover 20 extends radially beyond wound treatment volume 24 so that a second perimeter 68 is greater than a first perimeter 71. This generates a reflex transition portion 74 construction which may be adopted to increase the "length" and amount of material in the reflex transition portion 74.

Figure 11C:
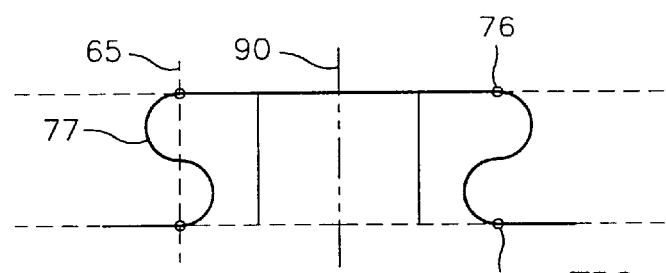
FIG. 11C is a schematic drawing depicting an alternate geometry for the transition portion.

FIG. 11C shows a construction where a first perimeter 76 and a second perimeter 78 have approximately the same value and are both concentric with an axis 90. This construction can produce an undulated transition portion 77. Once again, the length of undulated transition portion 77 exceeds the length of a line 65 between first perimeter 76 and second perimeter 78.

Figure 11D:
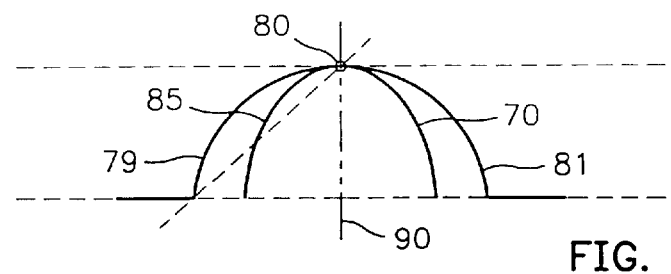
FIG. 11D is a schematic drawing depicting an alternate geometry for the transition portion.

FIG. 11D shows a hemispheric shell 70 as wound treatment portion 14. In this embodiment a second perimeter 80 is a single line of attachment that is generally concentric with axis 90. In this embodiment, a first perimeter 81 has a length which greatly exceeds the length of second perimeter 80. This construction forms a hemispheric transition portion 79 which has a length which exceeds the linear distance between second perimeter 80 and first perimeter 81 along a line 85.

Although the various geometries vary in detail, it is preferable to form transition portion 16 from a resilient material which is generally self-supporting, yet sufficiently flexible so that it acts as a compliant hinge mechanism. This flexibility substantially limits the transfer of shearing force from wound treatment portion 14 to attachment portion 12 of the wound treatment device 10, and visa versa. With the geometries set forth in FIG. 11A through FIG. 11D, transition portion 16 of wound treatment device 10 forms a shaped flexion joint or formed expansion joint which stores "material" in a pleat, convolution, bellows, or the like. This type of structure provides a means for expanding the size of transition portion 16 resulting in minimizing the transfer of forces from attachment portion 12 to wound treatment portion 14.

FIG. 12A through FIG. 14B should be considered together. In these embodiments of the invention, the standoff structure reduces in height resulting in increased transition portion projected area 17 during the stretching of the wound treatment device.

Figure 12A:
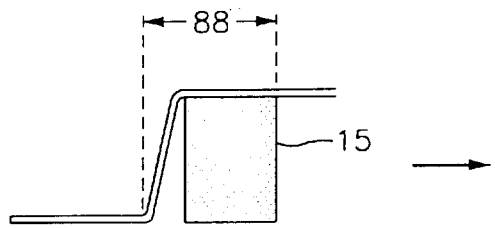
FIG. 12A is a schematic drawing depicting functional relationships between several elements of the invention.
Figure 12B:
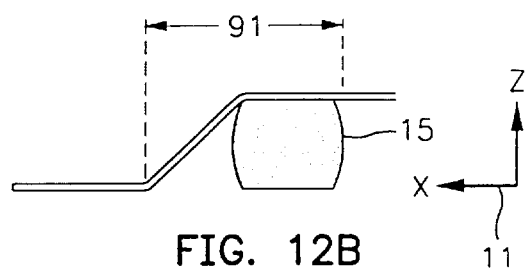
FIG. 12B is a schematic drawing depicting functional relationships between several elements of the invention.

FIG. 12A shows a part of a wound treatment device having foam ring standoff 15 in the unstressed or relaxed state. In this instance, transition portion projected area 17 is proportional to a dimension 88. In FIG. 12B, the wound treatment device has been stretched and the height of foam ring standoff 15 is reduced in the Z direction which has increased transition portion projected area 17 as represented by dimension 91.

Figure 13A:
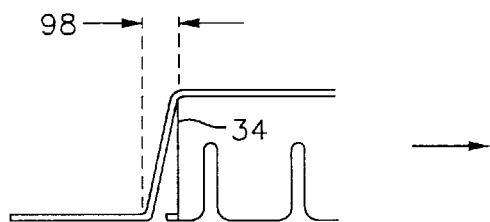
FIG. 13A is a schematic drawing depicting functional relationships between several elements of the invention.
Figure 13B:
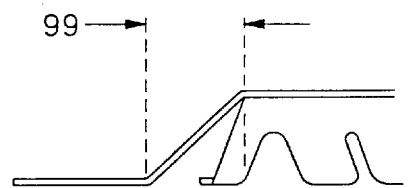
FIG. 13B is a schematic drawing depicting functional relationships between several elements of the invention.

FIG. 13A shows a part of a wound treatment device having serrated cup standoff 34 in the unstressed or relaxed state. In this instance, transition portion projected area 17 is proportional to a dimension 98. In FIG. 13B, the wound treatment device has been stretched, and the height of serrated cup standoff 34 is reduced in the Z direction. The serrated wall sections splay out to permit the height reduction which increases transition portion projected area 17 as represented by a dimension 99.

Figure 14A:
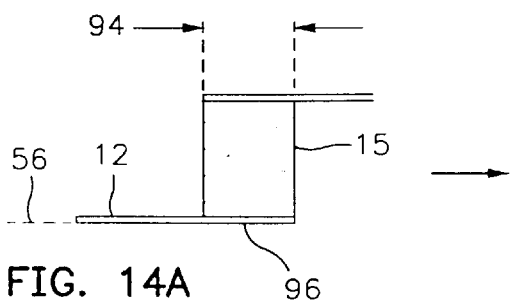
FIG. 14A is a schematic drawing depicting functional relationships between several elements of the invention.
Figure 14B:
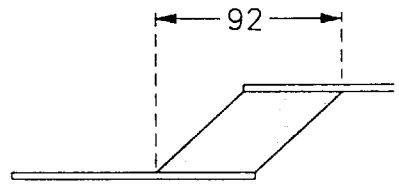
FIG. 14B is a schematic drawing depicting functional relationships between several elements of the invention.

FIG. 14A shows a part of a wound treatment device having foam ring standoff 15 in the unstressed or relaxed state. However, in this construction attachment portion 12 and a transition portion membrane 96 lie entirely in first plane 56. In this instance, transition portion projected area 17 is proportional to a dimension 94. In FIG. 14B, the wound treatment device has been stretched and the height of the foam ring standoff 15 is reduced in the Z direction. This height reduction increases transition portion projected area 17 represented by a dimension 92.

A flexible, non-contact wound treatment device is illustrated in FIGS. 15–19B where the same reference numerals specify identical parts throughout the drawings.

Figure 15:
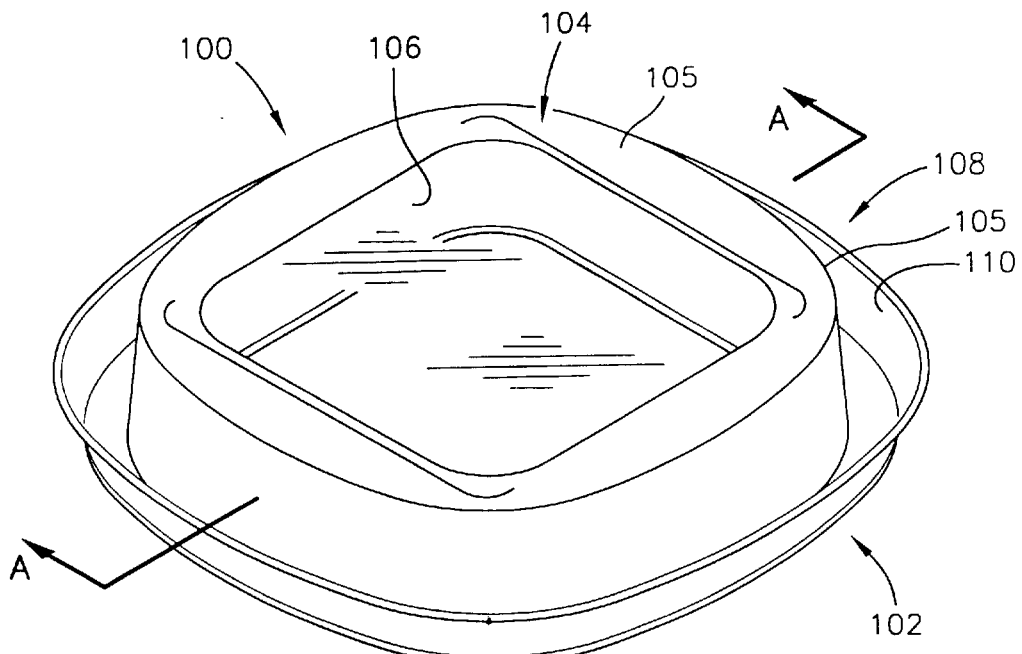
FIG. 15 is a perspective view of an embodiment of a flexible non-contact wound treatment device.

FIG. 15 is a perspective view of a flexible, non-contact wound treatment device 100 for application to a patient's skin surface. An attachment portion 102 is formed as a collar or flange. This attachment portion 102 is for attachment around a wound through an adhesive layer on the underside of the attachment portion. The embodiment of wound treatment device 100 also embraces a wound treatment portion 104 that includes a wound cover 105, described below, supported by a support member in the form of a standoff 106. A transition portion 108 connects the wound treatment portion 104 to the attachment portion 102 and preferably includes a membrane 110 that extends around an outer periphery of the support member 106 and is attached to the attachment portion 102 between inner and outer peripheries thereof.

Figure 17:
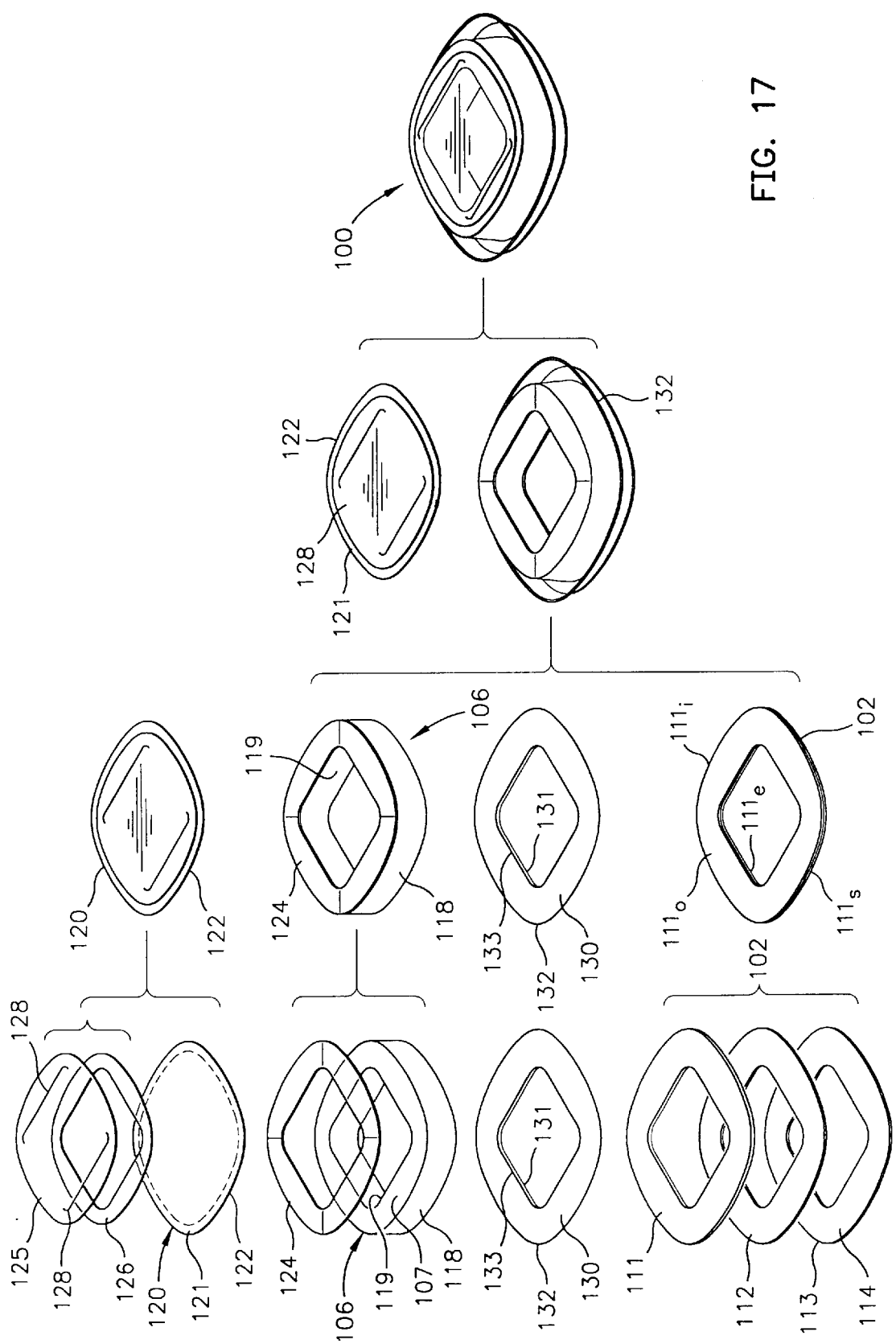
FIG. 17 is an exploded view of the embodiment of FIG. 15.

Referring now to FIGS. 15 and 17, in the wound treatment device 100, the attachment portion 102 is an integrated, unitary assembly preferably having three sections: a foam layer 111, an adhesive film layer 112 on a bottom surface of the foam layer 111, and a release liner 113 covering the adhesive film layer 112. One or more lines of weakness or perforation 114 are provided on the release liner 113 so that its parts may be separated and selectably peeled off of the adhesive film layer 112, thereby to expose the adhesive film layer 112 a section at a time for application to a person's skin. The foam layer 111 may comprise a naturally open-celled polyurethane foam. The foam layer 111 is preferably approximately 1/8" thick. The adhesive film layer 112 may comprise a high MVTR thin film, pressure sensitive adhesive (PSA) laminate available as a package under the trade name Mediderm from Bertek. The foam layer 111 is heat bonded to the adhesive film layer 112. The material of which the adhesive film layer 112 is comprised is selected for a combination of adhesion level, permeability, and conformability (stretching and flexing with the skin) to allow prolonged skin contact, without complications. The release liner 113 is a white release paper coated with a release agent that is provided on the Mediderm 3701 product. The perforations or slits 114 are made during assembly to aid in the removal of the release liner 113 prior to attachment of a wound treatment device to a person.

When 111, 112 and 113 are assembled, the attachment portion 102 is a flexible collar shaped part with an inner periphery portion 111i on an upper surface 111s of the foam layer 111 around an inner perimeter, or edge, 111e. The upper surface 111s faces, and is therefore disposed under, or beneath, the support member 106. The attachment portion 102 further includes an outer perimeter, or edge, 111o.

The wound treatment portion 104 includes the support member 106, which is preferably a ring of absorbent foam such as a naturally open-celled polyurethane foam that is selected to have favorable characteristics of absorbency, leaking and resevoiring. Such material is available as a product sold under the trade name Aquazone from Foamex. The support member 106 has an upper surface 107, a lower surface (109 in FIGS. 18B–19B), an outer perimeter, or edge, 118 and an inner perimeter, or edge, 119. The thickness of the support member 106 is preferably in a range extending from 1/2" to 5/8", with the exact dimension being selected to maintain non-contact at wound sites whereby, during use, the foam ring can compress and conform without the wound cover contacting the wound. The wound cover 105 in the preferred embodiment includes a layer 120 preferably of 4 mil.-thick clear, flexible polyurethane film with favorable characteristics selected, but not limited, to include moisture vapor transfer, oxygen permeability, and transmission of infrared radiation. Such material is available as a product sold under the trade name Deerfield 6100S. The layer 120 is attached to the upper surface 107 of the support member 106 by a ring 124 of adhesive comprising a synthetic rubber-base adhesive such the product sold under the trade name HL-2306-X by H. B. Fuller Adhesive. When the layer 120 is attached to the upper surface 107 of the support member 106, a perimeter portion 121 of the layer 120 extends out beyond the outer perimeter 118 of the support member 106. The wound cover 105 further includes a stretcher layer 125 attached to the layer 120 so that the layer 120 is sandwiched between the stretcher layer 125 and the upper surface 107 of the support member 106. The stretcher layer 125 is a 5 mil-thick planar sheet of (preferably) clear, somewhat flexible polyester film having enough stiffness to aid in maintaining planarity of the wound treatment portion 104. The function of the stretcher layer 125 is to hold the layer 120 taut, much as a "stretcher frame" tautens an artist's canvas. The stretcher layer 125 is attached to the layer 120 by a layer 126 of adhesive comprising a clear flexible polyester carrier film coated on both sides with an aggressive adhesive. The adhesive layer 126 is oriented over the support member 106. A film carrier allows for the adhesive to be run in a web process and die cut during manufacturing of the stretcher layer 125. The stretcher layer 125 further includes a pair of slits 128 that receive a detachable heater. With the provision of the slits 128, a pocket is formed between the stretcher layer 125 and the layer 120.

The transition portion 108 includes a lower collar 130 that is preferably formed from the same material as the layer 120. The transition portion 108 also includes the outer perimeter portion 121 of the layer 120 that extends out beyond the support member 106 when assembled thereto. When the wound treatment device 100 is assembled, a circumferential edge 122 of the layer 120 is joined to a corresponding circumferential edge 132 of the lower collar 130. Preferably, the edges 122 and 132 are sealed or welded together by a heat process. When so joined, the outer perimeter portion 121 of the layer 120 and the lower collar 130 form the membrane 110, which extends over the outside of the outer perimeter 118 of the support member 106. The lower collar has a ring-like shape that includes an inner periphery 131. An inner periphery portion 133 comprises an annular portion of the lower collar material on a surface of the lower collar that faces away from the lower surface 109 of the support member 106. The lower surface 109 is not shown in FIG. 17, but may be seen in FIGS. 19A and 19B.

The membrane 110 of the transition portion 108 is attached to the attachment portion 102 by heat-bonding or otherwise connecting the inner periphery portion 133 of the lower collar 130 at or near the opposing inner periphery portion 111i of the attachment portion 102.

Many variations of the assembly illustrated in FIGS. 15 and 17 are possible. For example, the support member 106 could be contained within the structure formed by the layer 120, lower collar 130, and attachment portion 102, unattached to any portion of the structure.

Figure 16:
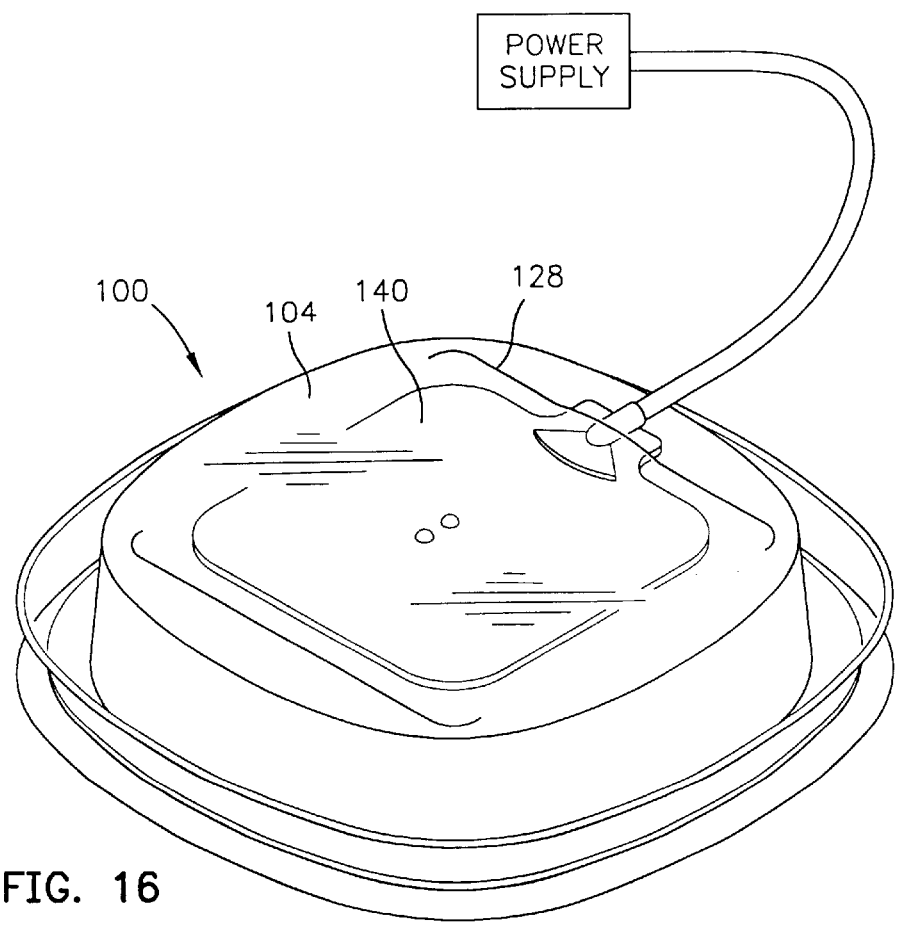
FIG. 16 is a perspective view of a detachable heater in combination with the embodiment of FIG. 15.

FIG. 16 shows a detachable heater 140 positioned on the wound cover 105 within a pocket formed between the layer 120 and the stretcher layer 125, with the opening to the pocket provided by one of the slits 128. The wound cover 105, with the heater 140 contained within the pocket, is supported substantially in a plane or surface above a wound by the support member 106. The heater 140 is generally planar and may be connected to and powered by a portable power supply such as that illustrated in FIG. 7.

Figure 18A:
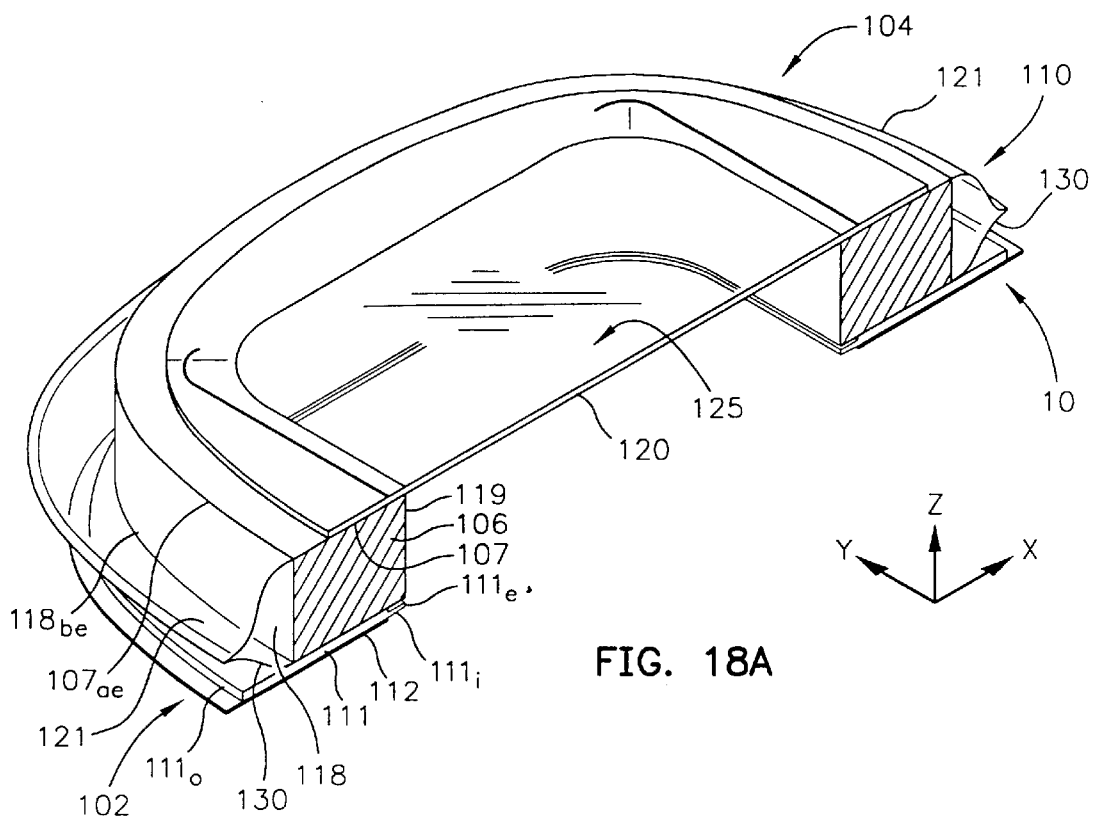
FIG. 18A is a cross-sectional perspective view of the embodiment of the FIG. 15 referred to A—A in FIG. 15.
Figure 18B:
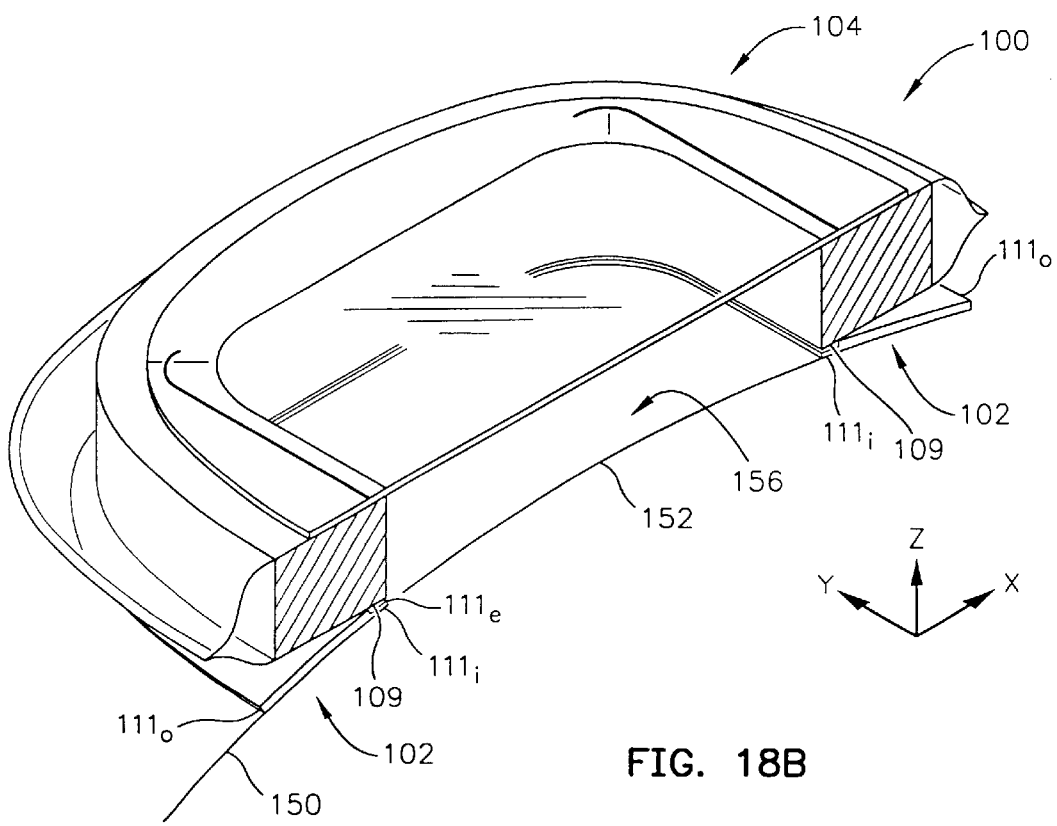
FIG. 18B is a cross-sectional perspective view of the embodiment of FIG. 15 showing the operation of a membrane in adapting the wound treatment device to body motion referred to A—A in FIG. 15.

Refer now to FIGS. 18–18C in which FIGS. 18A and 18B show details of the wound treatment device 100 when assembled and put in use. FIG. 18A illustrates the relationship of the attachment portion 102 with respect to the support member 106 of the wound treatment portion 104. In this regard, when the wound treatment device is assembled and placed on a flat surface, the attachment portion 102 and wound treatment portion 104 substantially align along the inner perimeters 119 and 111e.

The seal between the inner periphery portion 133 of the lower collar 130 and the inner periphery portion 111i of the attachment portion 102 lies beneath the lower surface of the support member 106. This is the surface that is indicated by reference numeral 109 in FIGS. 19A and 19B. Preferably, the seal joining the inner periphery portions 133 and 111i is a continuous, closed-loop seal. Although, for reasons explained below, this is the preferred location of the seal between the lower collar 130 and attachment portion 102, the inventors contemplate that the seal could comprise a substantially continuous, closed-loop trace anywhere between the outer perimeter 111o and inner perimeter 111e of the attachment member 102.

In FIGS. 17 and 18A, the seal between the edges 122 and 132 of the layer 120 and lower collar 130 is exaggerated as a flange. In practice, the shape of the membrane 110 extending from an upper outer edge 107ue of the upper surface 107 to a lower outer edge 118be of the outer perimeter 118 is rather elongated, with the flange much less pronounced than shown in FIG. 18A. Of course, the membrane 110 in the extent from the edge 107ue all the way down to the seal that joins the inner periphery portions 133 and 111i is not attached, and is therefore free from, although in close proximity to, the outer perimeter 118, lower edge 118be and lower surface 109 of the support member 106.

Referring now to FIGS. 18B–19B, the flexible, non-contact wound treatment device 100 is suitable for placement onto a skin surface 150 of a patient or person so as to include a selected wound area 152 that abuts a treatment volume 156 within the treatment device 100. This attachment may be directly to the skin surface 150, or on another member such as an ostomy ring that is, in turn, mounted or attached to the skin surface 150. As FIGS. 18B–19B demonstrate, the flexible, non-contact wound treatment device 100 of this invention satisfies the objective previously stated by a capability of being conformably attached to an uneven, changing surface supporting a wound treatment portion 104 that remains reasonably or substantially planar in its shape, regardless of body contour or movements. In this regard, as FIGS. 18B and 19B illustrate, the attachment portion 102 operates as a hinge or flexion joint that pivots at the seal between the inner periphery portions 133 and 111i. Relatedly, the attachment portion 102 is free to conform to the shape of the skin surface by flexibly deforming between the inner and outer perimeters 111e and 111o. At the same time, the wound treatment portion 104 is relatively undeformed so that the support member 106 is able to support the layer 120 and stretcher layer 125 in a relatively planar orientation with respect to the wound area 152. In the meantime, the wound treatment device 100 forms a barrier between the wound treatment v6lume 156 and the ambient atmosphere by virtue of the seal between the edges 122 and 132 of the layer 120 and lower collar 130, and the seal between the inner periphery portions 133 and 111i. The bottom of the wound treatment device 100 is sealed to the skin 150 when the release layer 113 is peeled off so that the adhesive film layer 112 seals to the skin surface 150.

FIGS. 18C and 19B illustrate the conformability of the wound treatment device 100 provided by flexion of the membrane 110 in the transition portion 108. FIGS. 18C and 19B are "snap shots" of the flexible, non-contact wound treatment device 100 after placement as described above with reference to FIGS. 18B and 19A and after movement of a body part on which the device 100 is placed. In these figures, movement is accommodated by excess length in the membrane 110. In FIGS. 18C and 19B, the membrane 110 has tensioned along the perimeter 118 to provide strain relief between the lower edge 118be of the support member 106 and the seal between the inner periphery portions 133 and 111i. In addition, the flexibility of the membrane 110 and its freedom from the outer perimeter 118 and lower surface 109 permit a play out of excess length of the membrane 110 that abuts the outer perimeter 118 of the support member 106. This moves the membrane 110 into close touching engagement with the outer perimeter 118, while lengthening the amount of membrane 110 available between the lower edge 118be and the inner periphery portion 111i.

In another aspect, as FIGS. 18C and 19B show, the membrane 110 acts as a double hinge or a double pleat between the lower edge 118be of the support member 106 and the attachment portion 102. A first hinge pivot or pleat is at the seal between 133 and 111i. This hinge permits the attachment portion to pivot toward and away from the wound treatment portion. The second hinge—at edge 118be—allows the wound treatment portion to move toward and away from the attachment portion. Manifestly, the same effect could be achieved by attachment of the membrane 110 to the lower surface 109 inside of the edge 118be.

Three significant advantages result from placement of the attachment portion 102 beneath the support member 106 of the wound treatment portion.

First, in plan, the shapes and extents of the bottom surface 109 and the attachment portion 102 align and largely overlap, thereby reducing the "foot print" of the wound treatment device 100 to a single, substantially annular shape from the two concentric shapes of FIGS. 2 and 3.

Next, the double hinge (or pleat) provided by the membrane 110 increases the conformability of the wound treatment device to shape and movement, while maintaining the planarity of the wound cover and preventing its contact with a wound.

Last, the lower collar 130, in extending substantially to the inner perimeter 111e of the attachment portion 102 forms a barrier to moisture and wound exudate which may be absorbed by the support member 106, thereby reducing maceration of skin underneath the attachment portion 102.

The Invention

Figure 20:
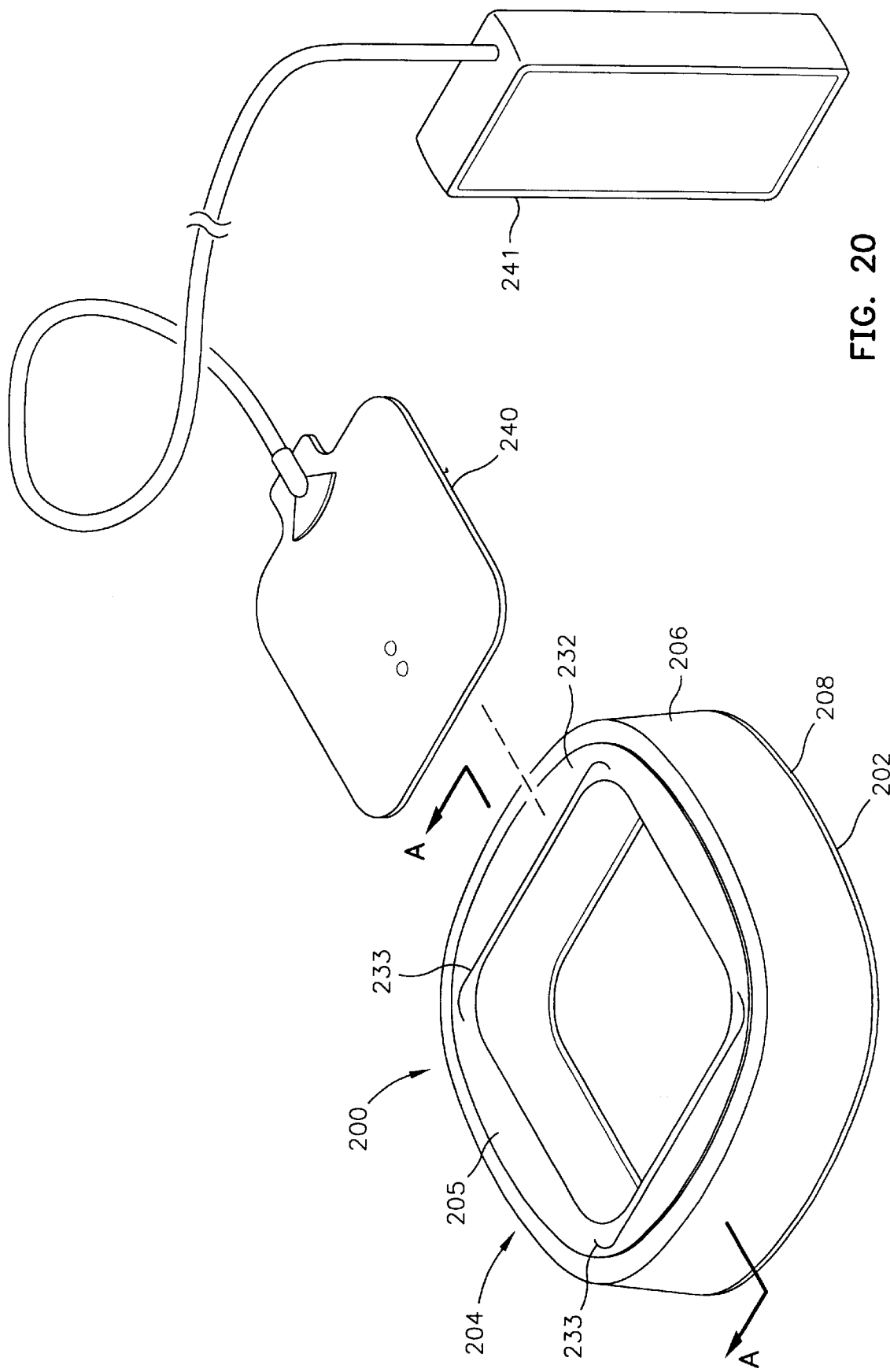
FIG. 20 is a perspective view of our invention, embodied as a flexible non-contact wound treatment device with a single flexion joint.
Figure 21:
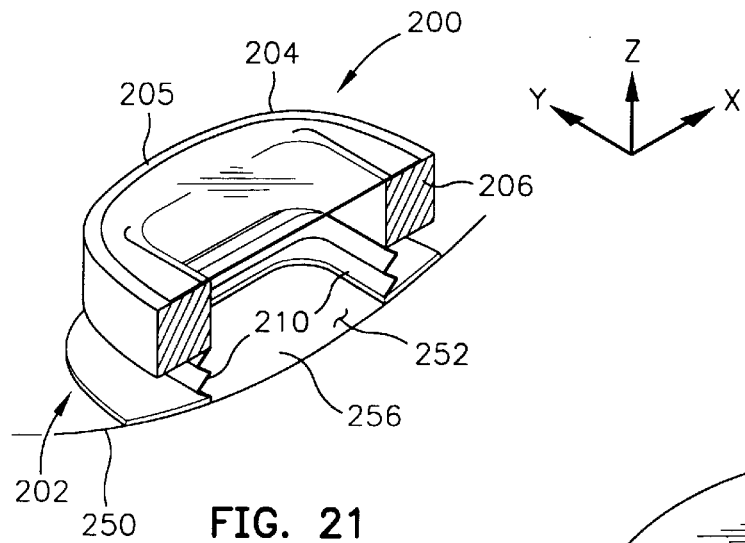
FIG. 21 is a cross-sectional perspective view of a first preferred embodiment referred to A—A in FIG. 20.
Figure 22:
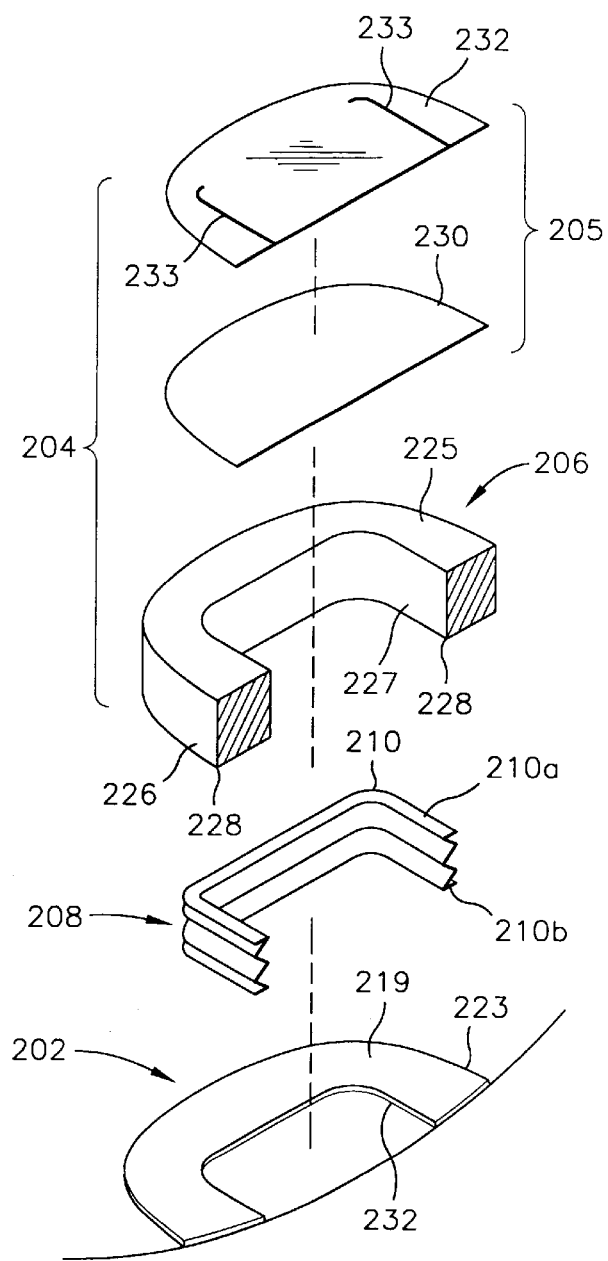
FIG. 22 is an exploded view of the cross-sectional illustration of the first embodiment.
Figure 23:
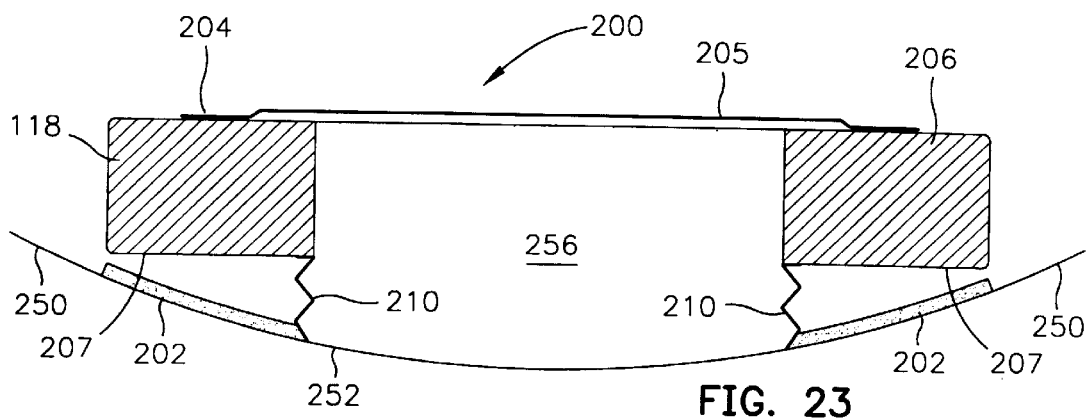
FIG. 23 is a cross-sectional side view of the first embodiment, when attached to a human patient.
Figure 26A:
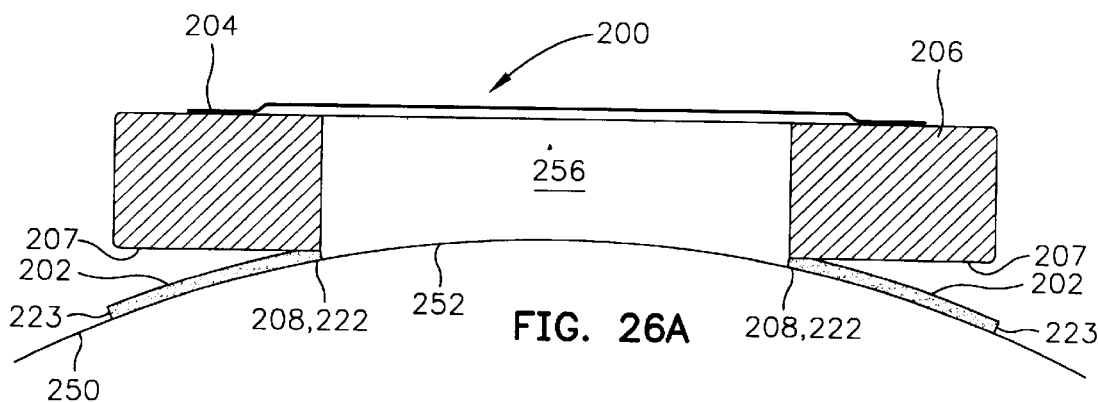
FIGS. 26A, B, and C are cross-sectional side views of the second embodiment when attached to a human patient.
Figure 26B:
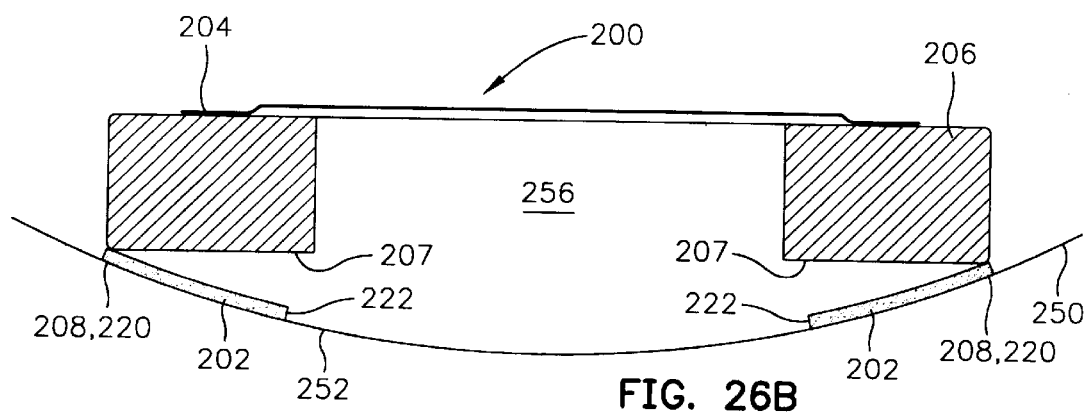
Figure 26C:
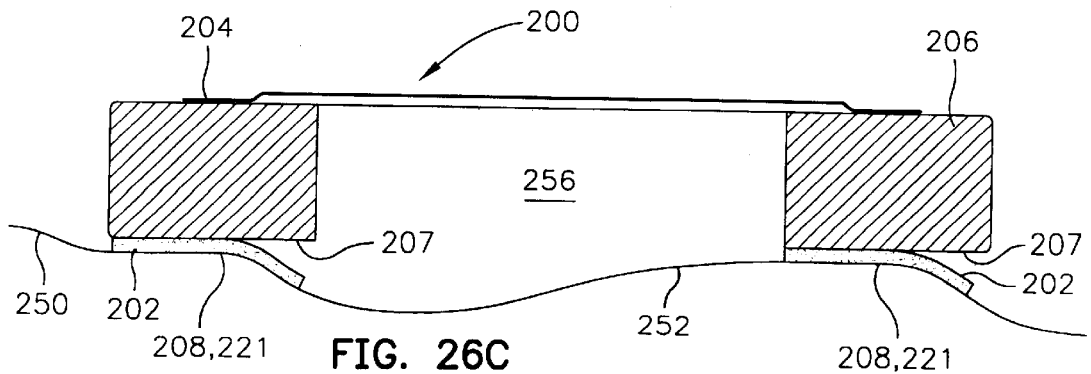
Figure 27:
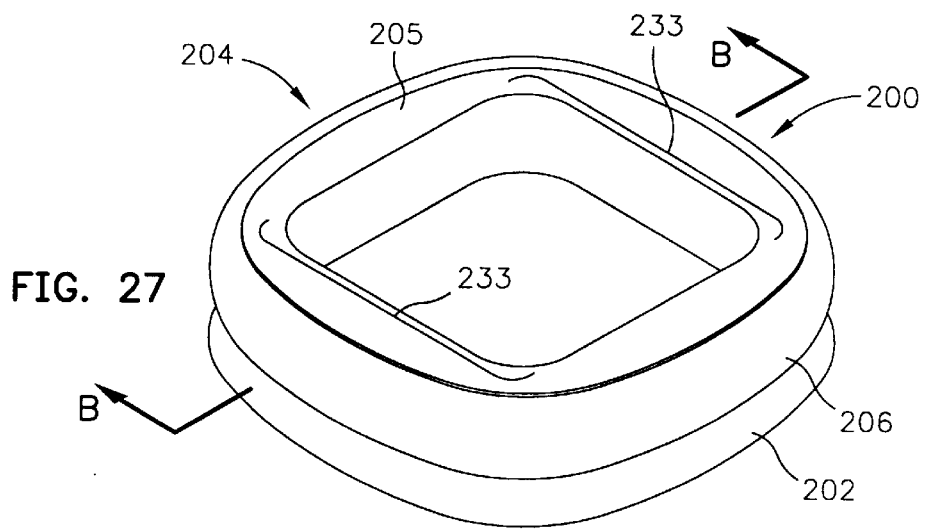
FIG. 27 is perspective view of a third preferred embodiment.
Figure 28:
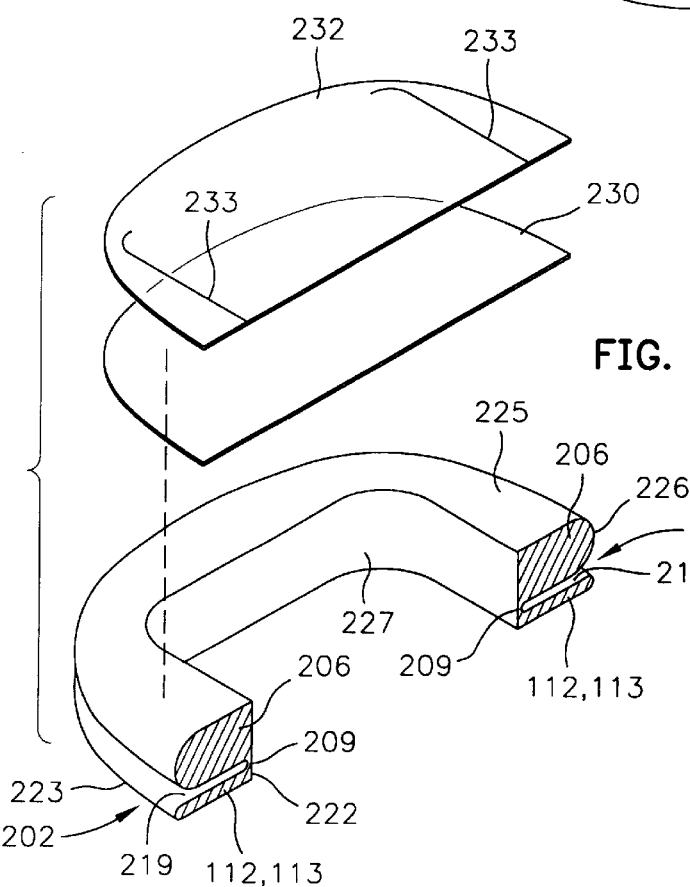
FIG. 28 is a cross-sectional perspective view of a third preferred embodiment referenced to B—B in FIG. 27.
Figure 29:
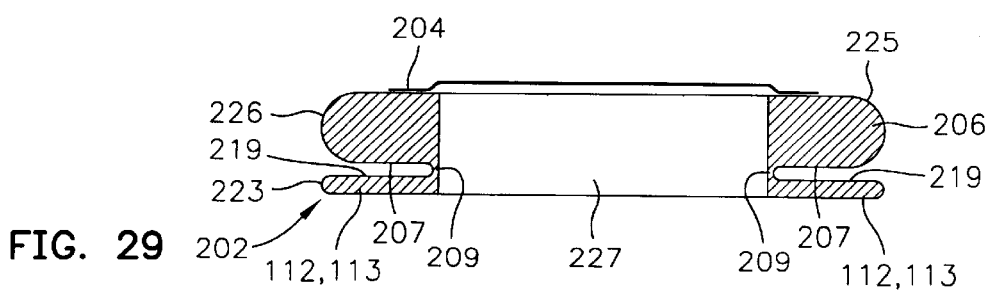
FIG. 29 is a cross-sectional side view of the third embodiment.

Our flexible, non-contact wound treatment device with a single joint is illustrated, in perspective, in FIG. 20. A first preferred embodiment of our invention is illustrated in FIGS. 21–23, a second embodiment is illustrated in FIGS. 24–26A, B and C and a third embodiment is illustrated in FIGS. 27–29. Among these embodiments, identical reference numerals specify identical parts throughout the drawings.

FIG. 20 is a perspective view of the flexible, non-contact wound treatment device 200 for application to a patient's skin surface. An attachment portion 202 is formed as a collar or a flange. This attachment portion 202 is for attachment to a patient's skin around a wound by way of an adhesive layer on the underside of the attachment portion. Our preferred embodiment of the wound treatment device 200 also embraces a wound treatment portion 204 that includes a wound cover 205, described below, supported by a support member in the form of a standoff 206. A transition portion 208 with a single joint, described below with reference to two preferred embodiments, connects the wound treatment portion 204 to the attachment portion 202.

In a first embodiment, illustrated in FIGS. 21 and 22, the transition portion 208 comprises a joint embodied as a pleated member 210. The pleated member 210 comprises multiple stacked pleats so that it assumes an accordion- or bellows-like configuration that operates between a lower surface of the standoff 206 and an upper surface 219 of the attachment portion 202.

Figure 24:
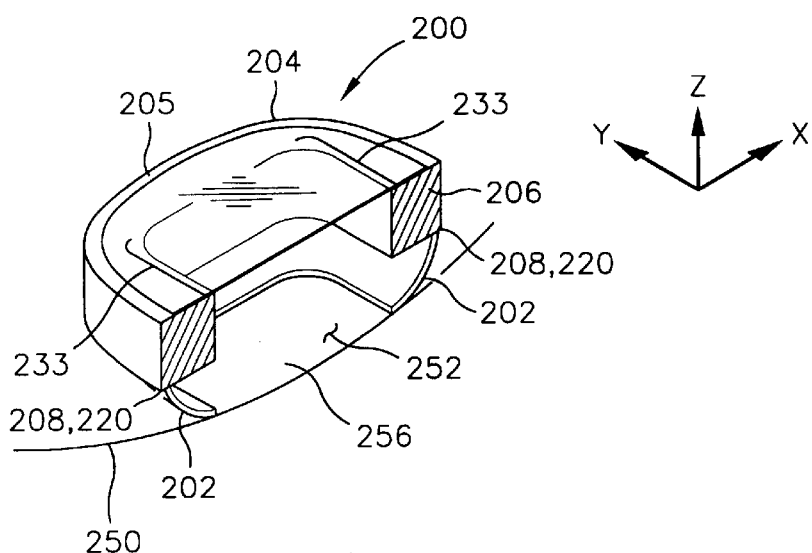
FIG. 24 is a cross-sectional perspective view of a second embodiment referred to in A—A in FIG. 20.
Figure 25:
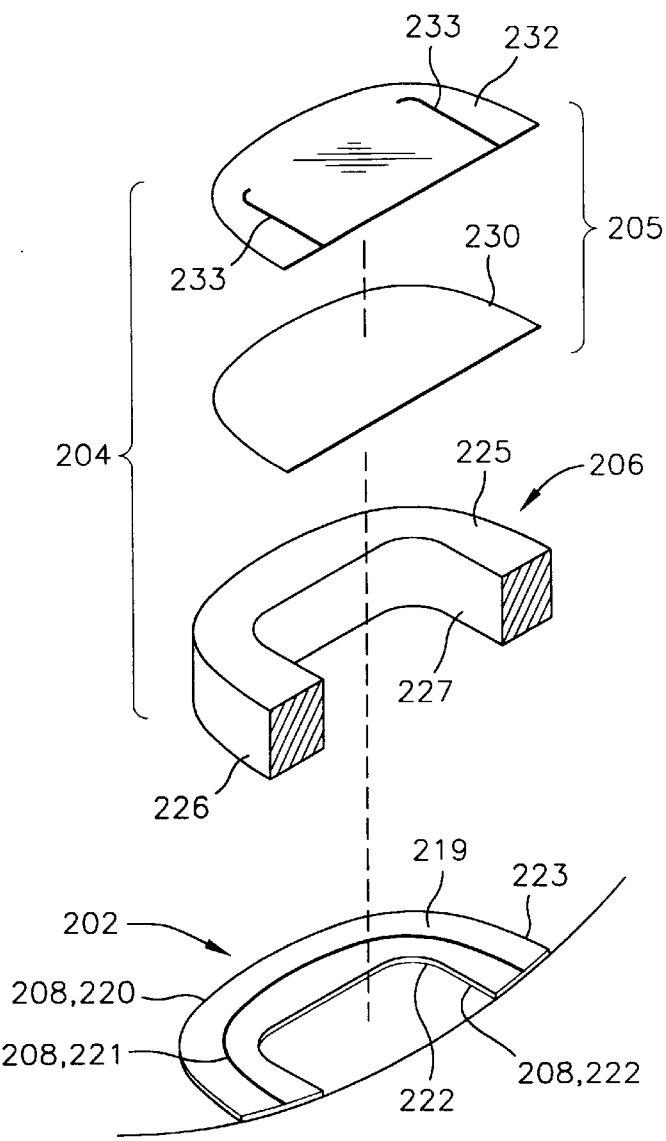
FIG. 25 is an exploded cross-sectional view of the second embodiment.

In a second embodiment illustrated in FIGS. 24, 25 and 26 the transition portion 208 comprises a single joint in the form of a substantially continuous seam formed by glueing, heat-welding, or any other equivalent and appropriate attachment procedure between the upper surface 219 of the attachment portion 202 and the lower surface of the standoff 206. Such a seam may be positioned, as preferred, on the surface 219 between inner and outer perimeters of the attachment portion 202. Three exemplary traces showing the location of the seam with respect to the upper surface 219 are indicated by 208/220, by 208/221, and by 208/222.

In a third embodiment, illustrated in FIGS. 27–29, the transition portion 208 comprises a "living hinge" in the form of a narrow bridge 209 of foam material in a preferably continuous annulus that spans and provides a hinge between attachment portion 202 and the lower surface of the standoff 206. Such a bridge may be positioned, as preferred, between the attachment portion 202 and the standoff 206 within the inner and outer perimeters of the attachment portion 202. Although only a single exemplary location of the bridge is shown, it is to be understood that many other locations would also be possible.

Referring now to FIGS. 22 and 25, in the wound treatment device 200, the attachment portion 202 is an integrated, unitary assembly preferably having the three sections, the properties, and the operations described above with reference to FIGS. 15 and 17. In this regard, the attachment portion 202 is a flexible, collar-shaped part with an inner perimeter 222 and an outer perimeter 223. The upper surface 219 of the attachment member 202 faces, and therefore is disposed under, or beneath, the support member 206, facing its lower surface.

The wound treatment portion 204 includes a support member preferably in the form of the standoff 206, which is preferably a ring of absorbent foam. Such foam may comprise, for example, naturally open-celled polyurethane foam that is selected to have favorable characteristics of absorbency, leaking and resevoiring. Preferably, the foam may be of the type known as "self-skinning foam." Such material is available as products sold under the trade names Aquazone and P100Z, from Foamex. Typically, self-skinning foam forms a non-permeable skin when molded. Thus the upper surface 225, the outer surface 226, and the lower surface of the standoff 206 (not shown, but oppositely-directed from the upper surface 225) are "skinned", while the center of the standoff 206 is die cut to expose the open cell structure on the inner surface 227. Thus, the inner surface 227 has the desirable property of absorbency (among others) described above with reference to the standoff of the wound treatment devices illustrated in FIGS. 1–19. The thickness of the standoff 206 is preferably in a range extending from ½" to ⅝", with the exact dimension being selected to maintain non-contact at wound sites whereby, during use, the standoff 206 can compress and conform without the wound cover contacting the wound. Alternatively, if a high moisture-vapor transission rate (MVTR) is desirable, the outer surface 226 may also be die cut exposing the open cells of the foam to the environment. Further, the standoff 206 may be altogether skinless if required.

The wound cover 205 includes a layer 230 preferably of 4 mil.-thick clear, flexible polyurethane film with favorable characteristics selected, but not limited, to include moisture vapor transfer, oxygen permeability, and transmission of infrared radiation. Such material is available as a product sold under the name Deerfield 6100S. The layer 230 is attached to the upper surface 225 of the support member 206 by a ring of adhesive (not shown) comprising a synthetic rubber-based adhesive such as the product sold under the trade name HL-2306X by H. B. Fuller Adhesive. When the layer 230 is attached to the upper surface 225 of the support member 206, its edge or perimeter is substantially flush with the edge or perimeter formed in the upper surface 225 by the outer surface 226. The wound cover 205 further includes a stretcher layer 232 attached to the layer 230 so that the layer 230 is sandwiched between the stretcher layer 232 and the upper surface 225 of the standoff 206. The stretcher layer 232 is preferably a 5 mil.-thick planar sheet of (preferably) clear, somewhat flexible polyester film having enough stiffness to aid in maintaining planarity of the wound treatment portion 204. The function of the stretcher layer 232 is to hold the layer 230 taut, much as a "stretcher frame" tautens an artist's canvas. The stretcher layer 232 is attached to the layer 230 by a layer of adhesive (not shown) comprising a clear flexible polyester carrier film coated on both sides with an aggressive adhesive. The stretcher layer 232 further includes a pair of slits 233 that receive a detachable heater. With the provision of the slits 233, a pocket is formed between the stretcher layer 232 and the layer 230.

Many variations of the materials and shapes of the elements thus far described are within the contemplation of the inventors.

With reference again to FIG. 20, a detachable heater 240 may be positioned on, or in, the wound cover 205 within the pocket formed therein, with the opening to the pocket provided by either of the slits 233. The wound cover 205, with the heater 240 contained within the pocket, is supported substantially in a plane or surface above a wound by the support member 206. The heater 240 is illustrated as being planar, but may comprise other shapes. Preferably, the heater 240 is connected to and powered by a portable power supply 241. When the heater 240 is received within the pocket and powered by the power supply 241, heat treatment of a wound by radiation through a treatment volume formed by the support member 206 and the wound cover 205 may be provided as described above.

Referring again to FIGS. 22 and 25, first and second embodiments of the transition portion 208 are illustrated. It is understood that these embodiments are only representative of the general principle of providing a joint between the attachment portion 202 and the wound treatment portion 204 that acts between the bottom surface of the standoff 206 and the top surface 219 of the attach nient portion 202. FIGS. 21, 22, 24, and 25 are cross-sectional perspective views of the first and second embodiments taken along lines A—A of FIG. 20.

With reference to FIGS. 21 and 22, the first embodiment of a flexible non-contact wound treatment device with a joint acting between the attachment and wound treatment portions includes a joint embodied by the pleated member 210. The pleated member 210 is adhered, bonded, or otherwise attached along an upper edge 210a to the bottom surface of the standoff 206. The pleated member 210 is attached along a lower edge 210b by adhesive, heat bonding, or other appropriate means to the top surface 219 of the flexible attach rnent member 202. Preferably, as shown in FIG. 21, the pleated member 210 is attached to the lower surface of the standoff 206 near an inner perimeter 228 where the lower surface transitions to the inner surface 227. Similarly, the pleated member 210 is preferably attached to the upper surface 219 of the attachment portion 202 near the inner perimeter 222. This is shown clearly in FIGS. 21 and 23. Nevertheless, the pleated member 210 could be dimensioned to be attached between the attachment and wound treatment portions 202 and 204 along any closed-looped trace between the lower surface of the standoff 206 and the upper surface 219 of the attachment portion 204. Preferably, the pleated member comprises a urethane film which may be molded or extruded to form the multiple stacked pleats shown in the figures.

Manifestly, construction details of the wound treatment device may result in the pleated member 210 being connected indirectly to either, or both, of the standoff and attachment portion. However, as long as the pleated member acts between these or equivalent elements in the location shown and for the purpose described, it will meet the definition of the invention.

As shown in FIGS. 21, 22 and 23, the flexible, non-contact wound treatment device 200 with a transition portion 208 in the first embodiment in the form of a pleated member 210 is suitable for placement onto a skin surface 250 so as to surround a selected wound area 252 that abuts a treatment volume 256 enclosed or contained within the wound treatment device 200. This attachment may be directly to the skin surface 250, or on another member such as an ostomy ring that is, in turn, mounted or attached to the skin surface 250. As FIGS. 21 and 23 illustrate, the flexible, non-contact wound treatment device 200 of this invention satisfies the objective previously stated by a capability of being conformably attached to an uneven, changing surface supporting a wound treatment portion 204 that remains reasonably or substantially in its original shape, regardless of body contour or movements. In this regard, as FIGS. 21, 22 and 23 illustrate, the attachment portion 202 operates as a flexion joint that flexes to adapt to the contour of the skin surface 252. In addition, the transition portion 208 in the form of the pleated member 210 supports relative movement between the attachment and wound treatment portions 202 and 204, permitting them to move toward and away from each other, and also parallel to each other, thereby enhancing the conformability of the wound treatment device 200 to contour and movement of the body. Relatedly, the attachment portion 202 is free to conform to the shape of the skin surface 250 by flexibly deforming between the inner and outer perimeters 222 and 223. At the same time, the wound treatment portion 204 is relatively undeformed so that the standoff 206 is able to support the layer 230 and stretcher 232 in a predetermined orientation with respect to the wound area 252. In the meantime, the wound treatment device 200 forms a barrier between the wound treatment volume 256 and the ambient atmosphere by virtue of the seal between the wound cover 205 and the standoff 206, the skinned outer and lower surfaces of the standoff 206, and the seals between the pleated member 210 and the standoff 206 and attachment portion 202. The bottom of the wound treatment device 200 is sealed to the skin 250 when the release layer (not shown) is peeled off so that the lower adhesive film layer (not shown) of the attachment portion 202 seals to the skin surface 250.

The second embodiment of the transition portion 208 may be understood with reference to FIGS. 24, 25 and 26A–26C. In this regard, the transition portion comprises a seam acting between the lower surface of the standoff 206 and the upper surface 219 of the attachment portion 202. Three possible seam locations are shown in FIG. 25. Such a seam may be formed by any appropriate means of attachment between the attachment portion 202 and the lower surface of the standoff 206. Such may include, without limitation, adhesive attachment, heat bonding, or any other appropriate measure.

As with the first embodiment of the joint, the inventors contemplate that a seam may be placed between other elements that effectively connect the seam to the attachment portion 202 and the lower surface of the standoff 206 in the location shown and for the purposes described.

The second embodiment of the transition portion 208 effectively allows articulation between the attachment portion 202 and the wound treatment portion 204. This is shown clearly in FIGS. 24 and 26A–26C. For example, in FIGS. 24 and 26B, the seal is in the location indicated by 208/220 in FIG. 25, essentially sealing an outer periphery of the upper surface 219 near the outer perimeter 223 to a corresponding outer periphery of the lower surface of the standoff 206. This permits the section of attachment portion 202 extending to the inner perimeter 222 to articulate toward or away from the lower surface of the stand off 206. FIG. 26A shows attachment of the attachment portion 202 along the seam 208/222 to the lower surface of the standoff 206 near the inner perimeter 222, where the section of the attachment portion 202 extending to the outer perimeter 223 can articulate toward or away from the lower surface of the standoff 206. FIG. 26C shows attachment of the upper surface 219 to the lower surface of the standoff 206 along the seam 208/221. In this location, the seam permits articulation of multiple sections of the attachment portion 202.

The third embodiment of the transition portion 208 may be understood with reference to FIGS. 2–29. In these figures, the transition portion comprises a bridge of foam material spanning and providing a narrow passage through the space between the bottom surface of the standoff 206 and the top surface 219 of the attachment portion 202. The bridge 209 is provided during the manufacture of the standoff 206 and the attachment portion 202 as an integrated, unitary piece by, for example, molding open-celled plastic foam of the self-skinning type. In this case, the bridge 209 is provided for in the mold and forms concurrently and integrally with the standoff 206 and the attachment portion 202. After molding, an adhesive fil m layer with an attached release liner 112, 113 (both described above with respect to the wound treatment device illustrated in FIGS. 15–17) may be attached to the lower surface of the attachment portion for application of the wound treatment device to a skin surface. Manifestly, the bridge 209 may be selectively located between the inner and outer perimeters 222 and 223 of the attachment portion 202 as with the first and second embodiments described above. In all other respects, the wound treatment device of FIGS. 27–29 is substantially identical with the wound treatment devices in FIGS. 20–26C.

As with the second embodiment, the bridge 209 effectively allows articulation between the attachment portion 202 and the wound treatment portion 204.

Three significant advantages result from placement of a joint beneath the standoff 206 of the wound treatment portion 204.

First, in plan, the shapes and extents of the bottom surface of the standoff 206 and the attachment portion 202 align and largely overlap, thereby reducing the "footprint" of the wound treatment device 200 to a single, substantially annular shape (which may be many-sided or circular), from the concentric shapes of FIGS. 2 and 3.

Next, the joint acting between the lower surface of the standoff 206 and the upper surface 219 of the attachment portion 202 increases conformability of the wound treatment device 200 to shape and movement, while maintaining the predetermined shape of the wound cover 205 and preventing its contact with the wound.

Last, the joint acting between the lower surface of the standoff 206 and the upper surface 219 of the attachment portion 202 forms a barrier to moisture and wound exudate which may be absorbed by the inner surface 227 of the standoff 206, thereby reducing maceration of the skin underneath the attachment portion 202.

While the invention has been illustrated by means of specific embodiments and examples of use, it will be evident to those skilled in the art that many variations and modifications may be made therein without deviating from the scope and spirit of the invention. However, it is to be understood that the scope of the present invention is to be limited only by the appended claims.

What is claimed is:

1. A non-contact wound treatment device, comprising:
    a flexible attachment portion having an opening defined by a closed perimeter;
    a support member having an opening;
    the attachment portion and support member openings aligned to form a wound treatment volume; and
    a joint connecting the support member and attachment portion; and
    the joint positioned between a surface of the support member and a surface of the attachment portion that overlaps and faces the surface of the support member, the joint permitting relative movement between the support member and the attachment portion.

2. The non-contact wound treatment device of claim 1, wherein the joint comprises a pleated member attached to the surface of the support member and to the surface of the attachment portion.

3. The non-contact wound treatment device of claim 1, wherein the joint comprises a seam between the surface of the support member and the surface of the attachment portion.

4. The non-contact wound treatment device of claim 1, wherein the joint comprises a bridge of material between the surface of the support member and the surface of the attachment portion.

5. The non-contact wound treatment device of claim 1, wherein the support member and the attachment portion are annular.

6. The non-contact wound treatment device of claim 1, further including a wound cover on the support member, over the opening in the support member.

7. The non-contact wound treatment device of claim 6, further including a heater.

8. The non-contact wound treatment device of claim 7, wherein the wound cover and heater are substantially planar.

9. The non-contact wound treatment device of claim 8, wherein the joint comprises a pleated member.

10. The non-contact wound treatment device of claim 8, wherein the joint comprises a seam.

11. The non-contact wound treatment device of claim 8, wherein the joint comprises a bridge of material.

12. The non-contact wound treatment device of claim 1, wherein the surface of the support member is a lower surface and the surface of the attachment member is an upper surface.

* * * * *

Disclaimer 6,267,740—Scott D. Augustine, Bloomington; John P. Rock, Minneapolis, both of MN. FLEXIBLE NON-CONTACT WOUND TREATMENT DEVICE WITH A SINGLE JOINT. Patent dated July 31, 2001. Disclaimer filed October 14, 2003, by the assignee, Augustine Medical, Inc.

The term of this patent shall not extend beyond the expiration date of Pat. No 6,110,197.

*(Official Gazette, March 2, 2004)*